Figure 1:
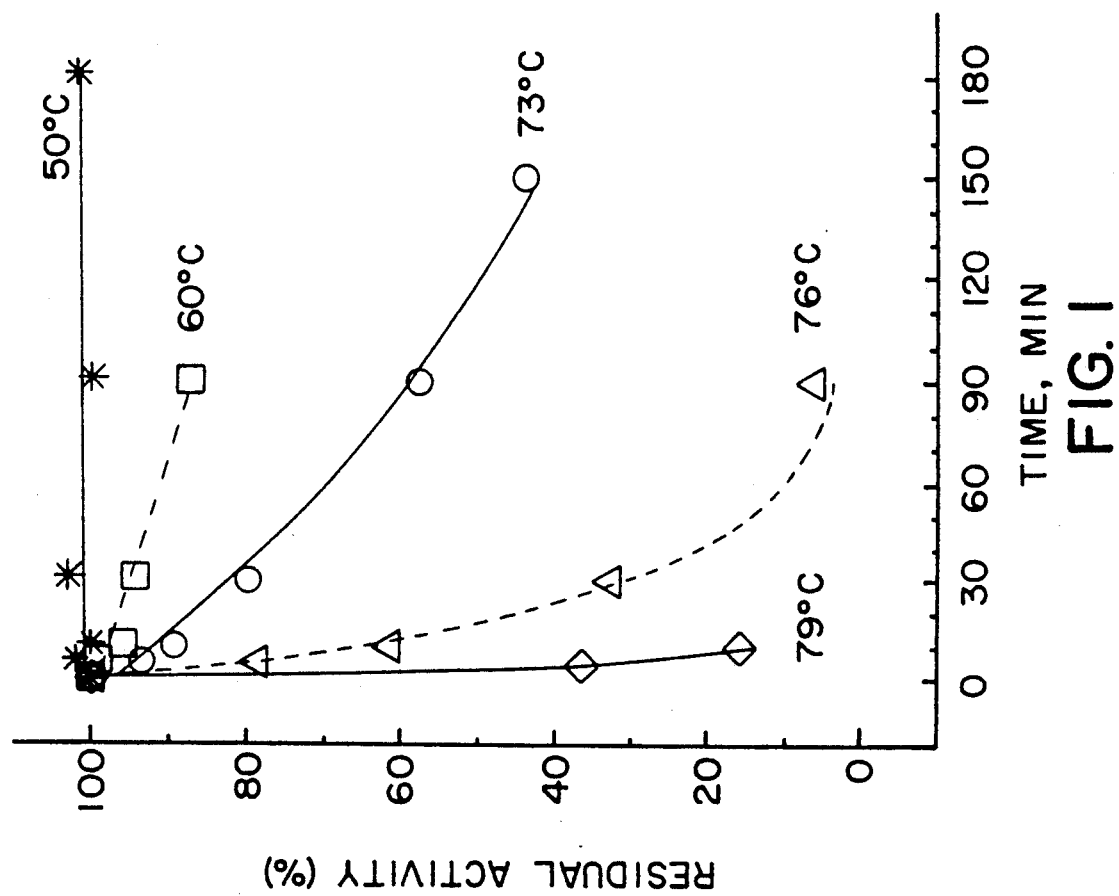

United States Patent [19]

Mrabet et al.

[11] Patent Number: 5,290,690
[45] Date of Patent: Mar. 1, 1994

[54] METHODS AND MEANS FOR CONTROLLING THE STABILITY OF PROTEINS

[75] Inventors: Nadir Mrabet, Koekelberg; Ignace Lasters, Perk; Patrick Stanssens, St.-Denijs-Westrem; Gaston Matthyssens, St.-Genesius-Rhode; Shoshana Wodak, Brussels, all of Belgium; Wilhelmus J. Quax, Voorschoten, Netherlands

[73] Assignees: Plant Genetic Systems, Brussels, Belgium; Gist-brocades, Delft, Netherlands

[21] Appl. No.: 398,706

[22] Filed: Aug. 25, 1989

[30] Foreign Application Priority Data

Jul. 15, 1988 [EP] European Pat. Off. ........ 88201539.9
Nov. 4, 1988 [EP] European Pat. Off. ........ 88402789.7
Jul. 17, 1989 [WO] PCT Int'l Appl. .................. PCT/EP89/00839

[51] Int. Cl.$^5$ .................... C07H 21/04; C12N 9/06; C12N 9/08; C12N 15/53
[52] U.S. Cl. .......................... 435/172.3; 435/69.1; 435/172.1; 435/191; 435/192; 536/23.2; 935/10; 935/14; 935/23
[58] Field of Search ............ 435/172.3, 69.1, 320.1, 435/172.1, 189, 195, 191, 192, 194; 935/23, 9, 10, 14; 536/27, 23.2

[56] References Cited

U.S. PATENT DOCUMENTS 4,410,627 10/1983 Lloyd et al. .......................... 435/94
4,904,584 2/1990 Shaw .................................. 435/69.4

FOREIGN PATENT DOCUMENTS 0028942 12/1982 European Pat. Off. ...... C12N 11/00

OTHER PUBLICATIONS

Shaw et al., *Protein Engineering* (Apr. 5-8, 1987) 1(3):264.
Rey et al., *Biol Abstracts* (1989) 87(6):AB-929, abstract No. 63577.
Argos, P. et al., "Thermal Stability and Protein Structure," *Biochemistry* 18(25):5698-5703 (1979).
Beyer, W. F. et al., "Examination of the Role of Arg-143 in Human Copper and Zinc Superoxide Dismutase by Site-Specific Mutagenesis." *J. Biol. Chem.* 262:11182-11187 (1987).

*Primary Examiner*—Robert A. Wax
*Assistant Examiner*—Dian Jacobson
*Attorney, Agent, or Firm*—Morrison & Foerster

[57] ABSTRACT

The invention pertains to a method for the production of a biologically active modified protein derived from a starting protein having essentially the same kind of biological activity with an attendant modulation effect on, particularly increase of, the stability as compared with that of the starting protein. The method comprises substituting an arginine residue for a lysine residue of the starting protein at a site that can sterically accommodate the substitution, without substantially altering the biological activity of the starting protein, said site being preferably of low solvent accessibility, at interfaces between domains or sub-units of the starting protein.

12 Claims, 35 Drawing Sheets

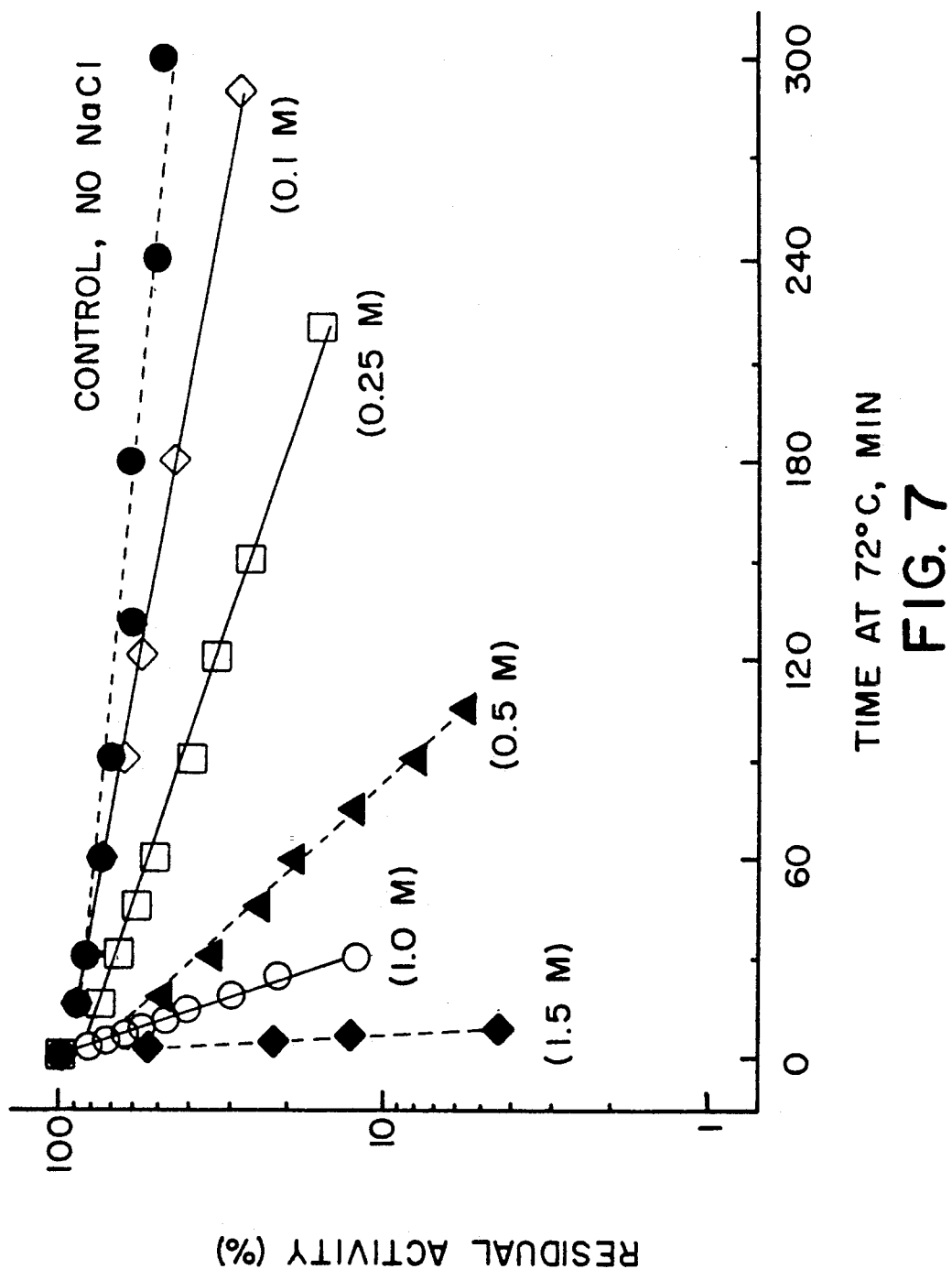

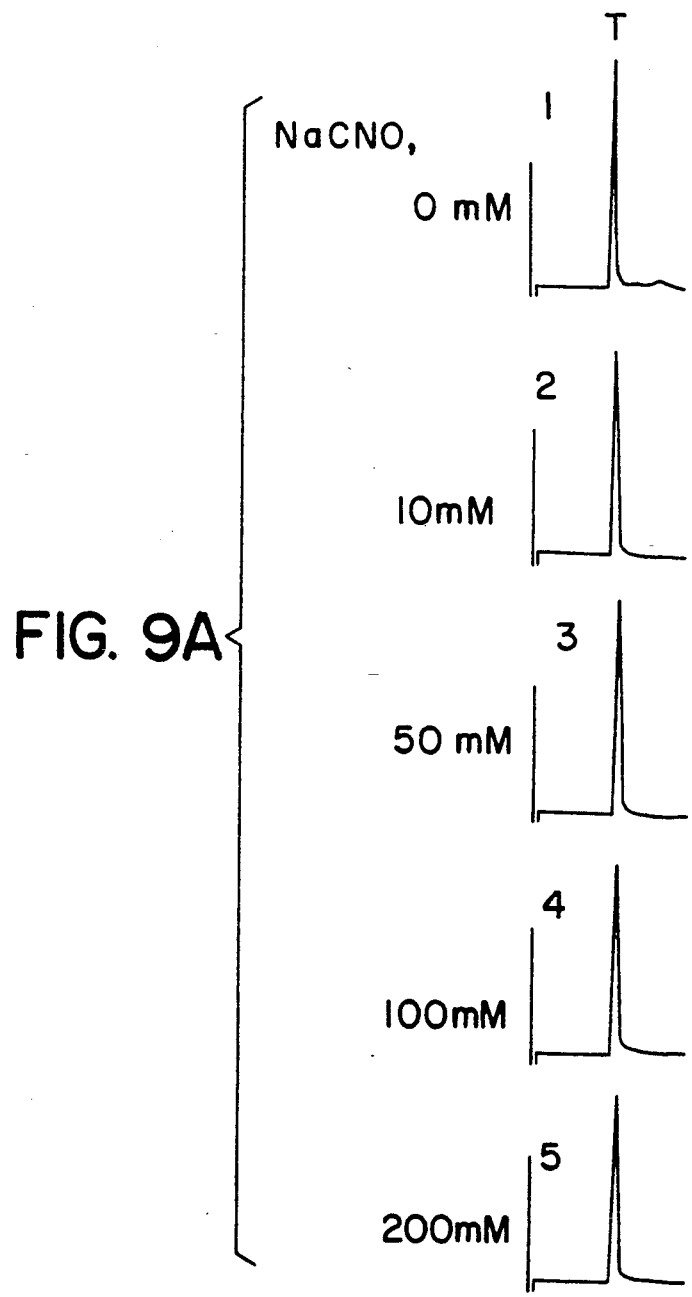

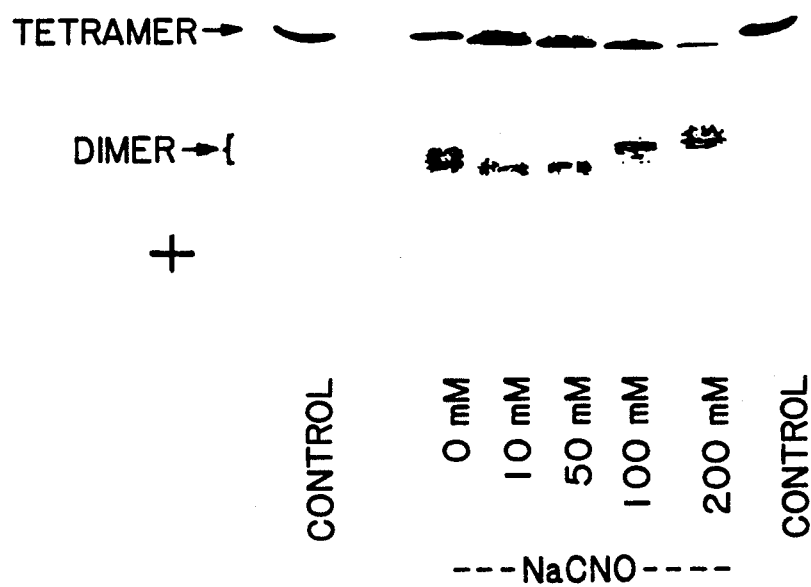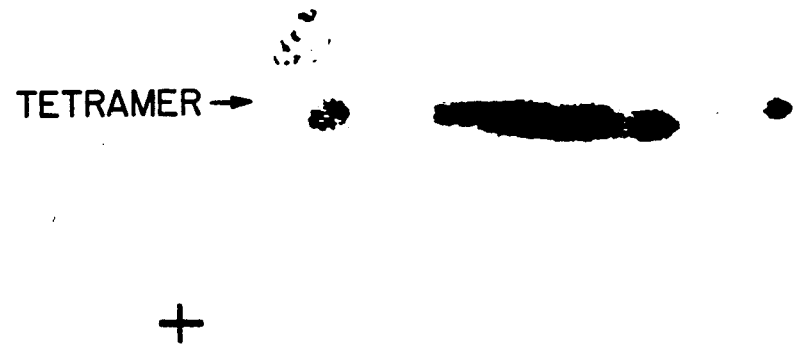
FIG.10B

```
GTG TCT GTC CAG GCC ACA CGC GAA GAC AAG TTC TCC TTC GGT CTC TGG ACC GTT
 V   S   V   Q   A   T   R   E   D   K   F   S   F   G   L   W   T   V
                                  27                                  54

GGA TGG CAG GCT CGT GAC GCG TTC GGT GAC GCC ACG CGT ACG GCA CTC GAC CCG
 G   W   Q   A   R   D   A   F   G   D   A   T   R   T   A   L   D   P
                                  81                                 108

GTC GAG GCC GTG CAC AAG CTC GCT GAG ATC GGT GCC TAC GGC ATC ACG TTC CAC
 V   E   A   V   H   K   L   A   E   I   G   A   Y   G   I   T   F   H
                                 135                                 162

GAC GAC CTG GTG CCC TTC GGC TCG GAC GCC CAG ACC CGC GAC GGC ATC ATC
 D   D   L   V   P   F   G   S   D   A   Q   T   R   D   G   I   I
                                 189                             216

GCC GGC TTC AAG AAG GCG CTC TTC ACC GAG ACC GGG CTG ATC GTC CCG ATG GTG ACC
 A   G   F   K   K   A   L   F   T   E   T   G   L   I   V   P   M   V   T
                                 243                                 270

ACC AAC CTC TTC ACC CAC CCG GTG TTC AAG GCG GGC TTC ACC AGC AAC GAC
 T   N   L   F   T   H   P   V   F   K   A   G   F   T   S   N   D
                                 297                             324

CGT TCC GTG CGG CGC TAC GCG ATC CGC AAG GTG CTG CGC CAG ATG GAC CTC GGC
 R   S   V   R   R   Y   A   I   R   K   V   L   R   Q   M   D   L   G
                                 351                                 378

GCC GAG CTG GGC GCC AAG ACG CTC GTC CTC TGG GGC GGC CGC GAG GGC GCC GAG
 A   E   L   G   A   K   T   L   V   L   W   G   G   R   E   G   A   E
                                 405                                 432
```

FIG. 15A

```
459
TAC GAC TCG GCC AAG GAC GTC AGC GCC GCC CTC GAC CGC TAC CGC GAG GCG CTC    486
 Y   D   S   A   K   D   V   S   A   A   L   D   R   Y   R   E   A   L

513
AAC CTG CTC GCG CAG TAC TCC GAG GAC CGC GGT TAC GGC CTG CTG CGC TTC GCC ATC    540
 N   L   L   A   Q   Y   S   E   D   R   G   Y   G   L   L   R   F   A   I

567
GAG CCG AAG CCG AAC GAG CCC CGC GGC GAC ATC CTG CTC CCG ACC GCC GGC CAC    594
 E   P   K   P   N   E   P   R   G   D   I   L   L   P   T   A   G   H

621
GCC ATC GCG TTC GTG CAG GAG CGT CCC GAG CTC TTC GGC ATC AAC CCG    648
 A   I   A   F   V   Q   E   R   P   E   L   F   G   I   N   P

675
GAG ACC GGG CAC GAG CAG ATG TCG AAC CTC AAC TTC ACC CAG GGC ATC GCC CAG    702
 E   T   G   H   E   Q   M   S   N   L   N   F   T   Q   G   I   A   Q

729
GCG CTG TGG CAC AAG AAG CTG TTC CAC ATC GAC CTG AAC GGT CAG CAC GGC CCG    756
 A   L   W   H   K   K   L   F   H   I   D   L   N   G   Q   H   G   P

783
AAG TTC GAC CAG GAC CAG GTC TTC GGC CAC GGT GAC CTG CTC AAC GCG TTC TCG    810
 K   F   D   Q   D   Q   V   F   G   H   G   D   L   L   N   A   F   S

837
CTG GTC GAC CTC CTG GAG AAC GGC CCG GAC GGC GCC CCG GCG TAC GAC GGA CCC    864
 L   V   D   L   L   E   N   G   P   D   G   A   P   A   Y   D   G   P
```

FIG. 15B

```
CGT CAC TTC GAC TAC AAG CCG TCC CGT ACC GAG GAC TAC GAC GGC GTC TGG GAG
 R   H   F   D   Y   K   P   S   R   T   E   D   Y   D   G   V   W   E
                         891                                         918

TCG GCG AAG GCC AAC ATC CGG ATG TAC CTG CTC AAG GAG CGG GCC AAG GCG
 S   A   K   A   N   I   R   M   Y   L   L   K   E   R   A   K   A
                         945                                         972

TTC CGC GCC GAC CCC GAG GTG CAG GAG GCG CTC GCC AGC AAG GTC GCG GAG
 F   R   A   D   P   E   V   Q   E   A   L   A   S   K   V   A   E
                         999                                        1026

CTG AAG ACC CCG AAC CTG AAC CCG ACC CTG AAC GGC GAG GGA TAC GCC GAG CTG CTC GCC GAC
 L   K   T   P   T   L   N   P   G   E   G   Y   A   E   L   L   A   D
                        1053                                        1080

CGC AGC GCG TTC GAG GAC TAC GAC GCC GAC GCC GTG GGC GCC AAG GGC TTC GGC
 R   S   A   F   E   D   Y   D   A   D   A   V   G   A   K   G   F   G
                        1107                                        1134

TTC GTC AAG CTG AAC CAG CTC ATC GAG CAC CTG CTC GGA GCC CGC TGA
 F   V   K   L   N   Q   L   I   E   H   L   L   G   A   R   *
                        1161                                        1188

FIG. 15C
```

```
                                    EcoRI
ACCGTGCGTTGACTATTTTACCCTCTGGCGGTGATAATGGTTGCATGTACTAAGGAGGTTGTATGGAAC
                                    |---->
AACGGCATAACCCTGAAAGATAGCTTGGGATCCGTCGACCGAGCAAATAATTCAACCACTAAACAAATCAA
                                    Start-GI
CCGCGTTCCCGGAGGTAACCGTGTCTGTCCAGGCCCACACGGGAAGACAAGTTCTCCTTCGTCTCTGGA

CCGTTGGATGGCAGGCTCGTGACGCGTTCGGTGACGCCACGCGTACGGGCACTCGACCGTCGAGGCCGT

GCACAAGCTCGCTGAGATCGGCCGCATCATCGGCCCTACGCGACGACTTCCACGACGACCCTTCGGCTCG

GACGCCCAGACCCGGACGGCATGGCCATCATCCGGGGCTTCAAGAAGCCGTCGACGAGACCCTGATCGTCC

CGATGGTGACCACCACCCTCTTCACCACCCGGTGTCAAGGCGGCTTCACCAACGACCGTTC

CGTGCGGGCGTACGCCGATCGCGCTGCCCAGTGACCTCGCCCGAGCTGCCCGAAGACG
```

FIG. 16A

```
CTCGTCCCTCGGGGCCCCGAGGGCCGAGTACGACTCGGCCAAGGACGTCAGCGCCCTCGACC
GCTACCCGAGGCCTCAACCTGCTCCCAGTACTCCGAGGACCGGGTACGCCTGGCGCTTCGCCAT
CGAGCCGAAGCCGAACGAGCCCCGGCGAACATCCTGCTCCCGACCGGCCACGCCATCCGGTCGTG
CAGGAGCTGGAGGCGTCCCCGAGCTCTTCGGCATCAACCCGGAGACCGGCAGCAGATGTCGAACCTCA
ACTTCACCCAGGCATCCCCCAGGCGCTGTGGGCACAAGAAGCTGTTCCACATCGACCTGAACGGTCAGCA
CGGCCCGAAGTCGACCAGGACCTGGTCTTCGGCCACGCCGTCAACGGTCGTTCGGCTGTGGTCGAC
CTCCTGGAGAACGACGCCCCCGACGGCTACGACGTCACTTCGACTACAAGCCGATCCTCGAAGCCGTCCC
GTACCGAGGACTACGAGGCGGTCGGAGTCGGAAGGCCAACATCCGGATGTACCTGCTCAAGGA
GCGGGGCCAAGGCGTTCCGCGACCCGGAGGTGCAGAGGCCTCGCCAGCAAGGTCGGGAGCTG
AAGACCCCGACCCTGAACCCTGAACGCCGAGGGGATACCGGCGCCGACCGCAGCCCGGTTCGAGGACT
```

FIG. 16B

ACGACGCCGACGCCCGTGGGGCCAAGGGCCTTCGGCTTCGTCAAGCTGAACCAGCTCGCGATCGAGCACCT

GCTCGGAGCCCGCTGACCATGGGCGTTGGTAGCCCGGATCGACAGCTCGACCCAGTCCTGCAAGGTCGTGA
<u>Stop</u>

TCCGGACGCCTGAGACAGGCCGCCGCTGGTCCCGGCAGGGCCGAGCCATCCCGGACGGCACCGAGGTGCA
         <---|

TCCGGACGCCTGGTGGTCGCCCGCTGCAGCTTGCAAGCTTGATTGATTGACCGGATCGATCCGGCTCTAGA

FIG. 16C

```
              10         20         30         40         50

CTGTTGACAA TTAATCATCG GCTCGTATAA TGTGTGGAAT TGTGAGCGGA 60         70         80         89
                                     >
TAACAATTTC ACACAGGAAA CAGGTAT ATG GCT ACG AAG GCT
                                MET Ala Thr Lys Ala 98          107         116         125
GTT TGT GTT TTG AAG GGT GAC GGC CCA GTT CAA GGT ATT
Val Cys Val Leu Lys Gly Asp Gly Pro Val Gln Gly Ile 134         143         152         161         170
ATT AAC TTC GAG CAG AAG GAA AGT AAT GGA CCA GTG AAG
Ile Asn Phe Glu Gln Lys Glu Ser Asn Gly Pro Val Lys 179         188         197     StuI 206
GTG TGG GGA AGC ATT AAA GGA CTG ACT GAA GGC CTG CAT
Val Trp Gly Ser Ile Lys Gly Leu Thr Glu Gly Leu His 215         224         233         242
GGA TTC CAT GTT CAT GAG TTT GGA GAT AAT ACA GCA GGC
Gly Phe His Val His Glu Phe Gly Asp Asn Thr Ala Gly 251         260         269         278         287
TGT ACC AGT GCA GGT CCT CAC TTT AAT CCT CTA TCC AGA
Cys Thr Ser Ala Gly Pro His Phe Asn Pro Leu Ser Arg 296         305         314         323
AAA CAC GGT GGG CCA AAG GAT GAA GAG AGG CAT GTT GGA
Lys His Gly Gly Pro Lys Asp Glu Glu Arg His Val Gly 332         341         350         359
GAC TTG GGC AAT GTG ACT GCT GAC AAA GAT GGT GTG GCC
Asp Leu Gly Asn Val Thr Ala Asp Lys Asp Gly Val Ala
```

FIG. 17A

```
     368          377          386          395          404
GAT GTG TCT  ATT GAA GAT  TCT GTG ATC  TCA CTC  TCA GGA
Asp Val Ser  Ile Glu Asp  Ser Val Ile  Ser Leu  Ser Gly 413          422          431          440
GAC CAT TGC  ATC ATT GGC  CGC ACA CTG  GTG GTC  CAT GAA
Asp His Cys  Ile Ile Gly  Arg Thr Leu  Val Val  His Glu 449          458          467          476
│AAA│GCA GAT  GAC TTG GGC │AAA│GGT GGA  AAT GAA  GAA AGT
│Lys│Ala Asp  Asp Leu Gly │Lys│Gly Gly  Asn Glu  Glu Ser 485          494          503          512          521
ACA AAG ACA  GGA AAC GCT  GGA AGT CGT  TTG GCT  TGT GGT
Thr Lys Thr  Gly Asn Ala  Gly Ser Arg  Leu Ala  Cys Gly 530          539          549          559          569
                                      StyI
GTA ATT GGG  ATC GCC CAA  TAAACATTCC CTTGGATGTA GTCTGAGGCC
Val Ile Gly  Ile Ala Gln 579          589          599
                                   SalI
CCTTAACTCA TCTGTTATCC TGCTAGTCGA C
```

FIG. 17B

Human CuZnSOD = HuSOD
Bovine CuZnSOD = BoSOD

```
HuSOD    1  ATKAVCVLKG DGPVQGiInF EqkesngpVk VwGSIkGLTE
            |||||||||| |||||| || |  ||  | |  ||||  ||||
BoSOD    1  ATKAVCVLKG DGPVQGtihF E  akgdtVv VtGSItGLTE HuSOD   41  GlHGFHVHeF GDNTaGCTSA GPHFNPLSrK HGGPKDEERH
            | |||||| | ||||  |||| ||||||||  | |||| ||||
BoSOD   39  GdHGFHVHqF GDNTqGCTSA GPHFNPLSkK HGGPKDEERH HuSOD   81  VGDLGNVTAD KdGVAdVsIe DsvISLSGdh cIIGRTlVVH
            |||||||||| | ||| | |  |  ||||| | |  |||| |||
BoSOD   79  VGDLGNVTAD KnGVAiVdIv DplISLSGey sIIGRTmVVH HuSOD  121  EKaDDLGkGG NEESTKTGNA GSRLACGVIG IAq
            || ||||| | |||||||||| |||||||||| ||
BoSOD  119  EKpDDLGrGG NEESTKTGNA GSRLACGVIG IAk
```

FIG. 18

```
         10         20         30         40         50         60         70
EcoRI
GAATTCGAGC TCGAGCTTAC TCCCCATCCC CCTGTTGACA ATTAATCATC GGCTCGTATA ATGTGTGGAA 80         90        100        110        120        130
TTGTGAGCGG ATAACAATTT CACACAGGAA ACAGGATCAA AGGAGGAAAC AATC ATG GCA GTA
                                         ↑                    MET Ala Val
                                                              139 148 175 184

AAA GTC GGT ATT AAC GGT TTT GGT CGT ATT GGA CGT AAC GTA TTC CGC GCA GCA
Lys Val Gly Ile Asn Gly Phe Gly Arg Ile Gly Arg Asn Val Phe Arg Ala Ala
193              202              211              220              229  238

TTA AAC AAT CCT GAA GTT GAG GTA GTA GCG GTT AAC GAT TTA ACA GAT GCT AAC
Leu Asn Asn Pro Glu Val Glu Val Val Ala Val Asn Asp Leu Thr Asp Ala Asn
247              256              265              274              283  292

ATG CTG GCT CAC CTT TTA CAA TAT GAT TCT GTA CAC GGA AAA TTA GAC GCT GAA
MET Leu Ala His Leu Leu Gln Tyr Asp Ser Val His Gly Lys Leu Asp Ala Glu
301              310              319              328              337  346

GTT TCA GTT GAC GGT AAC AAC CTT GTT GTT AAC GGC AAA ACA ATT GAA GTT TCT
Val Ser Val Asp Gly Asn Asn Leu Val Val Asn Gly Lys Thr Ile Glu Val Ser

FIG. 20A
```

```
     355        364        373        382        391        400
GCA GAA CGC GAT CCT GCT AAA CTT AGC TGG GGC AAA CAA GGC GTT GAA ATC GTA
Ala Glu Arg Asp Pro Ala Lys Leu Ser Trp Gly Lys Gln Gly Val Glu Ile Val 409        418        427        436        445        454
GTT GAA TCT ACT GGT TTC TTC ACA AAA CGC GCA GAC GCT GCG AAA CAC TTA GAA
Val Glu Ser Thr Gly Phe Phe Thr Lys Arg Ala Asp Ala Ala Lys His Leu Glu 463        472        481        490        499        508
GCT GGC GCG AAA AAA GTA ATC ATC TCT GCT CCT GCT AAC GAA GAT ATC ACA
Ala Gly Ala Lys Lys Val Ile Ile Ser Ala Pro Ala Asn Glu Asp Ile Thr 517        526        535        544        553        562
ATT GTT ATG GGT GTT AAC GAA GAT AAA TAC GAT AAC CAC GAT GTT ATC
Ile Val MET Gly Val Asn Glu Asp Lys Tyr Asp Ala Asn His Asp Val Ile 571        580        589        598        607        616
TCT AAC GCA TCT TGC ACA ACA AAC TGC CTT GCG CCG TTT GCA AAA GTA CTT AAC
Ser Asn Ala Ser Cys Thr Thr Asn Cys Leu Ala Pro Phe Ala Lys Val Leu Asn 625        634        643        652        661        670
GAT AAA TTC GGC ATC AAA CGC GGT ATG ATG ACA ACT GTT CAC TCT TAC ACA AAC
Asp Lys Phe Gly Ile Lys Arg Gly MET MET Thr Thr Val His Ser Tyr Thr Asn
```

FIG. 20B

|  |  |  |  |  |  |  |  |  |
|---|---|---|---|---|---|---|---|---|
| 679 | 688 | 697 | 706 | 715 | 724 |
| GAT | CAG | CAA | ATC | CTT | GAT | CTT | CCG | CAC | AAA | GAC | TAC | CGT | CGT | GCG | CGT | GCA | GCA |
| Asp | Gln | Gln | Ile | Leu | Asp | Leu | Pro | His | Lys | Asp | Tyr | Arg | Arg | Ala | Arg | Ala | Ala |
| | 733 | 742 | 751 | 760 | 769 | 778 |
| GCT | GAA | AAC | ATC | ATC | CCA | ACA | ACT | GGT | GCT | GCT | AAA | GCA | GTT | TCT | CTA | GTT |
| Ala | Glu | Asn | Ile | Ile | Pro | Thr | Thr | Gly | Ala | Ala | Lys | Ala | Val | Ser | Leu | Val |
| | 787 | 796 | 805 | 814 | 823 | 832 |
| CTT | CCT | GAA | CTA | AAA | GGC | AAA | GGT | AAC | GGT | GCT | ATG | CGT | GTT | CCA | ACT | CCA |
| Leu | Pro | Glu | Leu | Lys | Gly | Lys | Gly | Asn | Gly | Ala | MET | Arg | Val | Pro | Thr | Pro |
| | 841 | 850 | 859 | 868 | 877 | 886 |
| AAC | GTT | TCT | CTA | GTT | GAC | TTG | GTT | GCT | GAA | CTG | AAC | CAA | GAA | GTA | ACA | GCT | GAA |
| Asn | Val | Ser | Leu | Val | Asp | Leu | Val | Ala | Glu | Leu | Asn | Gln | Glu | Val | Thr | Ala | Glu |
| | 895 | 904 | 913 | 922 | 931 | 940 StyI |
| GAA | GTA | AAC | GCA | GCT | CTT | AAA | GAA | GCG | GCT | GAA | GGC | GAC | CTT | AAA | GGA | ATC | CTT |
| Glu | Val | Asn | Ala | Ala | Leu | Lys | Glu | Ala | Ala | Glu | Gly | Asp | Leu | Lys | Gly | Ile | Leu |
| | 949 | 958 | 967 | 976 | 985 | 994 |
| GAA | GAG | CCA | TTA | GTT | TCT | GGC | GAC | TAC | AAC | GGA | AAC | AAA | AAC | TCT |
| Glu | Glu | Pro | Leu | Val | Ser | Gly | Asp | Tyr | Asn | Gly | Asn | Lys | Asn | Ser |
| GGC | TAC | AGC | GAA | | | | | | | | | | | |
| Gly | Tyr | Ser | Glu | | | | | | | | | | | |

FIG. 20C

```
 1003          1012      1021      1030      1039      1048
              ClaI
         TCT ACA ATC GAT GCT CTT TCT ACA ATG GTT ATG GAA GGC AGC ATG GTA AAA GTA
         Ser Thr Ile Asp Ala Leu Ser Thr MET Val MET Glu Gly Ser MET Val Lys Val 1057          1066      1075      1084      1093      1102
         ATC TCT TGG TAC GAT AAC GAA AGC GGC TAC TCT AAC CGC GTT GTT GAC CTT GCA
         Ile Ser Trp Tyr Asp Asn Glu Ser Gly Tyr Ser Asn Arg Val Val Asp Leu Ala 1111          1120      1129      1142      1152      1162
                                       ^
         GCT TAC ATC GCA AAA AAA GGT CTT TAA TTTATAGCTG AAAAAGGACC TGACTTGGTT
         Ala Tyr Ile Ala Lys Lys Gly Leu 1172     1182       1192       1202       1212       1222       1232
 CTTTCGAATA GAAGCGCTAT AATGAAAGCG GACAAGGGAA GGGGACGGAC TCCCTTCCC TTTTTCCATG 1242     1252       1262       1272       1282       1292       1302
 AAGACCGGCT TTCAGAAAAC GCTCTCTGAT AGAGAAACGA CCGGCGTTTA AGCAGCTTTG CCGGCGCTTT 1312     1322       1332       1342       1352       1362
 AGACCTAAGGC CGCTGCCTGG CTTTTAGGCG AGCTGCCCTG TGCCGAAAAA GACTGCGATC CTCTAGA
                                                                     XbaI
```

FIG. 20D

1. BsuGAPDH = Bsu
2. BstGAPDH = Bst

```
Bsu    1    AVKVGINGFG  RIGRNVFRAA  LnNPevEVVA  VNDLTdAnmL
            ||||||||||  ||||||||||  | ||  ||||  ||||| |  |
Bst    1    AVKVGINGFG  RIGRNVFRAA  LkNPdiEVVA  VNDLTnAdgL

Bsu   41    AHLLqYDSVH  GkLDAEVsVd  gnnlvVNGKt  IeVsAERdPa
            ||||  ||||  | |||||  |            ||||  | ||| |
Bst   41    AHLLkYDSVH  GrLDAEVvVn  dgdvsVNGKe  IiVkAERnPe Bsu   81    kLsWGkqGVe  IVVESTGfFT  KRaDAAKHLE  AGAKKVIISA
            | ||   ||   ||||||| ||  || ||||||||  ||||||||||
Bst   81    nLaWGeiGVd  IVVESTGrFT  KReDAAKHLE  AGAKKVIISA Bsu  121    PAneEdITiV  MGVNeDKYDa  anHdVISNAS  CTTNCLAPFA
            ||  | ||    |||| ||||      |||||||  ||||||||||
Bst  121    PAkvEnITvV  MGVNqDKYDp  kaHhVISNAS  CTTNCLAPFA Bsu  161    KVLndkFGIk  RGMMTTVHSY  TNdQqILDLP  HKDyRrARAA
            |||    |||  ||||||||||  || |  ||||  ||| | ||||
Bst  161    KVLhqeFGIv  RGMMTTVHSY  TNnQrILDLP  HKDlRgARAA Bsu  201    AEnIIPTsTG  AAKAVsLVLP  ELKGKLNGgA  MRVPTPNVSl
            || ||||  |  ||||| ||||  |||||||| |  ||||||||||
Bst  201    AEsIIPTtTG  AAKAVaLVLP  ELKGKLNGmA  MRVPTPNVSv Bsu  241    VDLVAELnqE  VTaEEVNAAL  KeAAEGdLKG  ILgYSEEPLV
            |||||||  |  || |||||||| | |||| |||  || ||||||||
Bst  241    VDLVAELekE  VTvEEVNAAL  KaAAEGeLKG  ILaYSEEPLV Bsu  281    SgDYNGnknS  STIDALSTMV  meGsMVKViS  WYDNEsGYSn
            | ||||   |  ||||||||||   | || | |   ||||| |||
Bst  281    SrDYNGstvS  STIDALSTMV  idGkMVKVvS  WYDNEtGYSh Bsu  321    RVVDLAAYIa  kKGL
            ||||||||||   |||
Bst  321    RVVDLAAYIn  aKGL
```

FIG. 21

METHODS AND MEANS FOR CONTROLLING THE STABILITY OF PROTEINS

The present invention is linked to the field of protein engineering and provides methods for the production of novel proteins with modified stability, preferably towards thermal denaturation and/or chemical modification, by means of one or more amino acid replacements at specific sites in proteins using protein engineering techniques.

The present invention further provides novel proteins and related genes produced by these methods.

BACKGROUND OF THE INVENTION

Proteins are chemical compounds endowed with tiological functions. Proteins with the ability to catalyze chemical reactions are designated enzymes.

Many proteins, especially enzymes from microbial sources, have found an extensive use in a variety of industrial applications. Enzymes have a number of advantages over purely chemical processes. They are highly specific, and can efficiently catalyze reactions which might otherwise require extreme conditions of e.g. temperature, pressure, pH, etc.

The following list is intended as a non-exhaustive list of particular examples. For a more detailed treatment of these and other industrial enzymes, reference is made to Godfrey and Reichelt (1983).

Amylases, glucose isomerases, glucoamylases, isoamylases, invertases, pullulanases, etc. are used in the starch conversion technology which is applied in the preparation of a great variety of products (Van Beynum and Roels, 1985).

Beta-galactosidases, catalases, chymosines, lipases etc. are used in the dairy industry.

Cellulases find an application in waste treatment industry.

Proteases are used in the detergent, the leather and baking industries.

Pectic enzymes are applied in the fruit juice industry

Glucose oxidase is used as an antioxidant in brewing and wine-making industries and in the food industry in general, and also finds applications in clinical diagnostics and analytical assays.

For industrial purposes either whole microbial cells or purified enzymes may be used. Purified enzymes, although more costly, are preferred because they can generally convert a higher proportion of substrate, while displaying fewer side reactions.

The use of enzymes in industry, and of proteins in general, is still restricted in many cases. The greatest technical difficulty is the finding of suitable proteins which are stable under industrially desired conditions such as temperature, pH, requirements of activators, and/or the presence of inhibitors.

Most industrial enzymes are used preferably at elevated temperatures so that contamination and viscosity are reduced while reaction rates are increased. However, at industrially preferred temperatures, proteins are bound to undergo inactivation. Therefore, industrial enzymes are often best derived from thermophilic microorganisms.

pH considerations must take into account the pH optimum of specific enzymes, the stability of substrate and products, and conditions further imposed by upstream and/or downstream operations in the industrial process.

Enzyme activators and coenzymes present a problem to the extent that they create additional costs e.g. for their elimination from the product during down-stream processing.

Inhibitors are a problem in as much as they can be difficult to remove from the reaction mixture or may be even essential for the reaction (e.g. in the case of substrate inhibition). Inhibitors can act through a variety of mechanisms, one of which is chemical modification of the protein.

The use of proteins for therapeutic applications is rapidly increasing, mostly due to developments in recombinant DNA technology. Recombinant tissue Plasminogen Activator, human serum albumin, human growth hormone, interferons, and insulin for instance are already well known in this respect (Watson et al., 1983; Roskam, 1987). Other examples are L-Asparaginase which finds an application in the treatment of acute lymphocytic leukemia, and superoxide dismutases which have been proposed for the treatment of oxidative damage in a wide variety of applications.

Last, but not least, a large variety of proteins are used for clinical or analytical assays (Bergmeyer, 1983), or as diagnostics (Dodet, 1987).

In all these applications where particular proteins are used, one is often confronted with the problem of protein stability Indeed, many proteins, particular enzymes, become unstable and inactivated when they are isolated from their natural environment.

Proteins commonly consist of combinations of some or all of twenty monomeric building blocks called amino acids. The amino acids are conventionally represented by either a three-or a one-letter code as shown in Table I.

The amino acids are linearly linked together by a special type of covalent bond termed the peptide bond. The order or sequence of the amino acids so linked is the primary structure of a protein. The primary structure is important for at least three reasons. First, it determines the three-dimensional (3D) structure of a protein. Second, it confers the latter three-dimensional conformation with one or more biological functions via the choice of amino acids necessary for the conformational structure yet bestowed with the appropriate chemical physical characteristics to fulfill the desired functionality. Third, essential information regarding the DNA sequence can be ascertained from the primary structure of a protein and vice versa.

A polypeptide is the amino acid chain that is translated from a single messenger RNA (mRNA) which, in turn, is transcribed from a single structural gene. Proteins are composed of one or more polypeptide chains. Monomeric proteins are composed of a single polypeptide chain (and in some cases, e.g. insulin, of a few covalently linked polypeptide chains). Oligomeric proteins are composed of two or more polypeptide chains, termed "subunits", which are structurally similar to monomeric proteins without necessarily possessing separate biological functions.

The three-dimensional structure of a protein comprises its secondary, tertiary, and quaternary structures. Secondary structure refers to structural elements that involve the relationship or interaction of the main-chain atoms of neighboring amino acids of the primary chain. Tertiary structure is the spatial arrangement of all atoms of the amino acids making the polypeptide chain. Many proteins may associate into super-assembly structures; in such multi-subunit proteins, the term quaternary Structure refers to the arrangement of subunits in the protein and quaternary interactions are those which occur between atoms belonging to different subunits.

Owing to secondary, tertiary, and quaternary structure, many complex interactions may occur between amino acids, whether they are close or far remote from each other within the amino acid sequence.

In the native state —i.e. the state associated with biological function—, the polypeptide chain adopts one, or a small number of, well defined conformations. In the denatured state, the protein is devoid of biological function; in this so-called "unfolded" state, the three-dimensional structure is not well defined in that the polypeptide chain assumes a large number of different conformations (Anfinsen & Sheraga, 1975).

The native state is stable under well defined conditions of pH, temperature, ionic strength and pressure. Where unfolding —denaturation— is shown to be reversible, it is verified that the free energy of the native state is lower than that of the denatured state. In such instance, the difference in free energy (delta G) between the two states provides a direct measure of protein stability (Privalov, 1979).

In addition to covalent interactions, the native conformation results from a complex interplay of different forces (Janin,1979):

1 Hydrophobic interactions, which are thought to be the most important contribution favoring the folded state in aqueous environment (Kauzmann, 1959; Privalov, 1979).
2. Chain entropy, i.e. the number of conformational states, which is the most important single contribution favoring the unfolded state.
3 Specific non-covalent interactions between protein atoms in the folded state, which at least compensate for similar interactions made with the solvent in the unfolded state. These are hydrogen bonds, Van der Waals interactions, and other electrostatic interactions between charges (ionised groups) and/or dipoles (Creighton, 1983).

Folding is the process that leads to the formation of the native state, whereas denaturation is the process which leads to the denatured (or unfolded) state starting from the native conformation.

The kinetics of the unfolding —or of the folding— process is, under given physical conditions, a function of the energy barrier encountered by the system during the transition process (Creighton, 1983). It is not a function of the difference in free energy between the native and denatured states.

In multi-subunit (oligomeric) proteins, individual subunits often display an appreciable degree of folding prior to their assembly into the final quaternary structure. The structure of the isolated subunits, however, need not be absolutely identical to that observed in the final oligomeric state. Upon recognition and association, further structural adjustments may indeed occur so that the final quaternary conformation acquires its most thermodynamically favored state (Jeanicke, 1987).

In polypeptide chains above a certain size (about 100 amino acid residues), the presence of globular sub-structures, termed "domains", has been recognized. Based on the analysis of a number of protein 3D structures (see review by Janin & Wodak, 1983), as well as on experimental data on protein renaturation (Goldberg, 1969), and on the discovery that such domains could be isolated by limited proteolysis (Porter, 1973), it is believed that domains could play an essential role in folding (Wetlaufer, 1973).

Structural domains can be identified in proteins with known 3D structures using the procedure described by Wodak and Janin (1981). In case the structure of a protein is not known, indications of domains can be obtained by studies on limited proteolysis (Porter, 1973).

It has been inferred from the above considerations that interactions between subunits or between domains contribute to increase the stability of the folded native state (Miller et al., 1987), and that folded individual domains, or subunits, can be folding intermediates. The early steps in protein denaturation are thus likely to involve the disruption of interactions between subunits or domains (Ptitsyn, 1987).

Such contention is in general widely and largely accepted by those experts in the art as a result of numerous observations derived from the study of naturally occurring protein mutants (Perutz, 1978; Walker et al., 1980; Mrabet et al., 1986).

Enzymes are proteins which have the ability to catalyze biochemical reactions. Enzymes are very specific for their substrate, a consequence of the 3D structure and of the physical-chemical properties of their "active site" where the substrate binds and the chemical reaction takes place (Fersht, 1985).

The partial or total loss of enzymatic activity (or of biological activity in proteins, in general) is termed inactivation. As a result of the above-mentioned considerations, any alteration of the native conformation of the enzyme may influence the enzymatic activity, and, in particular, lead to inactivation.

Thermal inactivation of enzymes, i.e. the loss of enzymatic activity as induced by temperature, may be either reversible or irreversible, depending on whether return to ambient temperature results in the recovery of biological activity within a reasonable period of time (Klibanov, 1983). The most common causes of irreversible denaturation are believed to be either non-covalent (aggregation or folding into a stable non-native conformation) or covalent (chemical modification of the covalent structure of the polypeptide chain). The latter has been shown to prevail in lysozyme (Ahern & Klibanov, 1985). A number of chemical reactions can take place in proteins at high temperature (Zale & Klibanov, 1986), but the most frequently studied ones are deamidation (Asn and Gln are converted to Asp and Glu, respectively), hydrolysis (e.g. cleavage of the acid-labile peptide bond following an Asp residue (Inglis, 1983), and oxidation of methionine to the sulfoxide form.

Covalent alterations of the protein structure —in particular, the introduction of chemical cross-links— can also impart protein stability. It has indeed been the most common means for increasing protein (thermo)stability in the past (Torchilin, 1983; Sadana & Henley, 1986; Gottschalk & Jaenicke, 1987). The success of this approach has however been limited because (1) the protocols rely on exhaustive screening of cross-linking agents of variable lengths and/or chemistry, (2) the chemical reactions cannot be reliably targeted to specific amino acid residues of the protein and may therefore occur at unwanted sites, such as those which may interfere with biological function.

More recently, with the advent of protein engineering, it has been possible, by site-directed mutagenesis (SDM) of the gene, to modify a given protein amino acid sequence at will, and thereby produce enzymes with improved properties (for reviews see Knowles, 1987, and Dill, 1987).

In some of the early examples, SDM has been used to engineer non-native disulfide bonds in proteins. Only in a limited number of cases, however, has this approach been successful (Perry & Wetzel, 1984; Wetzel, 1985; Sauer et al., 1986; Villafranca et al., 1983 and 1987; Wells & Powers, 1986; Pantoliano et al., 1987). Reasons for this modest success are reviewed and discussed by Wetzel (1987) and Creighton (1988).

A more stable variant of T4 phage lysozyme has also been obtained by substitutions of the type X for Gly and of the type Pro for X where X is any other amino acid, attributing that effect to the reduced conformational freedom of the mutant due to the presence of "stiffer" residues (Matthews et al., 1987).

SDM has been used recently to study hydrophobic stabilization of bacteriophage T4 lysozyme resulting in one variant with increased stability (Ile to Leu substitution at position 3 (Matsumura et al., 1988).

SDM has also been used to probe the nature of electrostatic interactions —hydrogen bonds and interactions between charged groups— and their influence on the pH dependence (Russel et al., 1987) and enzyme kinetic parameters of subtilisin (wells et al., 1987). But their influence on protein stability has not been investigated by this technique, nor has a more stable enzyme been produced as a result of specific modulation of electrostatic interactions.

The role of non-covalent interactions between protein subunits and/or domains has seldom been assessed by means of SDM. In a first example, Casal et al. (1987) could show that substitution of asparagine at position 78 by aspartic acid in dimeric yeast triosephosphate isomerase produced more labile protein. This result has been rationalized on the basis that deamidation of asparagine into aspartic acid is found to occur in proteins at elevated temperature. In a second example, simultaneous replacement of asparagine residues in the same model protein at positions 14 and 78 by threonine and isoleucine, respectively, was found to result in improved thermostability (Ahern et al., 1987). The doubling of the half-life of the mutant enzyme was, however, accompanied by a two-fold reduction in catalytic activity.

Temperature-sensitive mutations in bacteriophage T4 lysozyme were found to occur at sites of low solvent accessibility in the folded protein (Alber et al., 1987).

DESCRIPTION OF THE INVENTION

The present invention provides a method to control or modulate protein stability, preferably with respect to chemical modification or thermal denaturation or both, by mutation of lysine residues to arginine residues or by mutation of arginine residues to lysine residues.

The present invention thus provides a method to increase the stability of proteins by mutation of at least one lysine residue into an arginine and this at specific locations in the protein molecule.

In one preferred embodiment of the invention the substitution of arginine for lysine occurs at sites in the protein in which both residues are sterically accommodated in the 3D-structures of the protein whose stability is sought to be increased. At such sites, mutations of lysine residues to arginine residues can be intended to eliminate chemical modifications involving the epsilon amino group of lysine. In proteins, lysine residues, but less so arginines, are prone to chemical modification. Thus, the epsilon amino group in lysine is known to react with aldehydes and ketones to generate Schiff base adducts and further modification products, which eventually promotes the loss of biological activity (Holmquist & Schroeder, 1964; Bookchin & Gallop, 1968; Bunn et al., 1975, and 1978; Koenig et al., 1977; Higgins & Bunn, 1981). In particular, where lysine residues occur within interfaces between domains and/or subunits, chemical modification at such sites is likely to promote domain or subunit dissociation and/or to hamper the correct reassociation of the subunits and/or domains which are consequently irreversibly trapped in the dissociated state.

By substituting specific arginine residues for lysine residues, the extent of this chemical modification and its effect on protein activity and/or stability can be reduced. Consequently, a change of a lysine residue to arginine will improve the stability of the protein with respect to chemical modification.

Also, at sites which sterically accommodate the lysine to arginine mutations, a substitution of the arginine residues for the lysine residues will still result in an increased stability of the protein. This is because, due to the presence of the guanidinium group, the side chain flexibility for arginine is less than for lysine, so that mutation of lysine to arginine is favored on entropic grounds. Also the guanidinium group of arginine is capable of forming more numerous hydrogen bonds with neighbouring residues in the protein thus leading to improved stability.

In another preferred embodiment of the invention, particularly where enhancement of thermal stability is sought, at least one lysine residue occurring initially and particularly at a location of the type defined hereafter in the protein whose stability is sought to be increased is changed to arginine. The substitution of arginine for lysine is thought to improve the electrostatic interactions in which the substitute arginine residue then participates, particularly interactions within the interface between subunits and/or domains. In this embodiment, the lysine residue to be replaced should preferably comply with the following requirements and this with respect to the folded, native, protein conformation:

1. The residue to be replaced should be directly involved in electrostatic interactions, preferably in the interface between subunits an/or domains.
2. The mutation should occur at a site that can sterically accommodate the amino acid residue that is introduced.
3. The residue should occur at a site of low solvent accessibility and, preferably be part of an interface between subunits and/or domains.

Preferably, one should search for amino acid residues which, while fulfilling criteria (1) and (2), have the lowest ASA in the protein, simultaneously requiring that the ASA have values that are lower than the average determined for the given residues. In sites which satisfy these prerequisites, arginine, as compared to lysine, provides an improved electrostatic interaction due to the physical-chemical properties of its side-chain guanidinium group (see e.g. Wigley et al., 1987).

For the purpose of the present invention a residue is said to be located in the interface between subunits or domains whenever that residue loses solvent-accessible surface area upon domain (or subunit) association. The solvent accessibility surface (Lee & Richards, 1971) defines the surface of closest approach of the centers of solvent molecules with respect to the Van der Waals envelope of a protein. By low solvent accessibility of a given residue, it is meant that the computed (SURVOL algorithm, in the BRUGEL model-building package) accessible surface area (ASA) is less than the average determined for that residue in the ensemble of known protein structures (Rose et al., 1985).

For the purpose of the present invention, an electrostatic interaction is any interaction involving 1) charged groups such as carboxylates, tertiary amines, guanidinium groups, imidazole groups or charged heterogroups (e.g., metals —see also Bernstein et al., 1977) and/or 2) polar groups such as carbonyls, amino— or imino groups, hydroxyl groups, sulfhydryl groups, bound water or macrodipoles (Hol, 1985).

For the purpose of the present invention, a substitution is said to be sterically accommodated if any structural strain, such as short Van der Waals contacts, observed in the novel molecule derived by model building techniques, can be relieved by standard energy minimization procedures such as the "Steepest Descent" (Fletcher & Reeves, 1964), or "Conjugated Gradient" (Fletcher & Reeves, 1966) algorithms.

For the purpose of the present invention, it is generally desired to retain a substantial amount of biological activity of the proteins with modified stability as produced by the present invention. To retain such biological activity, the amino acid residues that are to be replaced should preferably not be those that have been identified as catalytic residues or as being substantially involved in cofactor binding. However, a decrease in biological activity can be tolerated, provided it is largely compensated for by the gain in stability achieved according to the present invention. In particular, a large decline in bioactivity is allowed if the mutated protein becomes functional at temperatures at which the wild-type protein expresses no activity at all.

The present invention also provides a method for decreasing the stability of proteins. The method essentially comprises the substitution of lysine for an arginine initially present in the starting protein at sites that meet some of the conditions required for the lysine to arginine mutations described above.

Thus for instance, at sites in the native protein (1) in which the residues concerned are involved in electrostatic interactions, preferably between subunits and/or domains, and (2) that have low solvent accessibility, the substitution of lysine for arginine will decrease the stability of this electrostatic interaction and consequently the stability of the protein. It may be noted that for the arginine to lysine substitution, the conditions with regard to steric accommodation of the new residue will not a priori appear a a restriction. This results from the fact that the shorter and more flexible side chain of the lysine residue is due to be well accommodated at a site originally occupied by arginine.

Also the substitution of a lysine for an arginine at sites that sterically accommodate any of the two residues will make the protein more susceptible to chemical modification by aldehydes and ketones, which may reduce the stability of the protein in environments that promote such chemical modifications.

It is clear that a specific amino acid substitution of the present invention can modify the stability of a protein by the combination of some or all of the effects mentioned above i.e. effects such as changing the strength of an electrostatic interaction, changing the number f hydrogen bonds with neighboring residues, by changing the conformational entropy of the protein or by influencing the extent of chemical modification.

A protein of the present invention can be produced by the methods of the present invention by the following general procedure. Specific lysine or arginine residues can be identified as candidates for replacement by careful examination of the three-dimensional structure of the protein, obtainable by methods such as crystallography (Wyckoff at al., 1985), or nuclear magnetic resonance spectroscopy (Wüthrich, 1986), or structure derivations based on available 3D-structures from homologous proteins (see e.g. Blundell et al., 1987), or from structure predictions based on analysis of the primary structure (for a review, see Taylor, 1988). The examination of the 3D structure of proteins can be performed by use of a dedicated computer software package such as the BRUGEL molecular graphics software package (Delhaise et al., 1984). Additional information on suitable residues can be obtained by a careful analysis of the mechanism or mechanisms involved in protein inactivation under specific denaturing conditions. Finally, the substitution of the amino acid residue, located at a preferred site can be achieved by conventional methods, particularly site directed mutagenesis of the DNA sequence encoding the protein using for example the vectors and procedures as described by Stanssens et al. (1987) and bacterial strains described by Zell and Fritz (1987).

The present invention also relates to novel proteins with modified stabilities obtainable by the methods described in the present invention, and to the genes that have been mutated so as to encode these proteins.

The proteins of the present invention can be obtained by constructing chimeric genes which comprise the modified genes linked to suitable expression signals such as appropriate promoter sequences, secretion signal sequences, ribosome binding sites, start and stop codons and transcription termination sequences for prokaryotic and eukaryotic cells, and appropriate polyadenylation signals for eukaryotic cells. The chimeric genes are further introduced in a host environment that enables their expression and/or replication such as prokaryotic or eukaryotic cells. The chimeric genes of the present invention can be engineered by conventional techniques (see e.g. Winnacker, 1987 and references therein) so as to be present in the host environment on a replicon of whatever nature such as plasmids, phages or even the genome of a host organism.

In this regard the present invention also relates to such chimeric genes, to replicons carrying these modified genes and to host environments that propagate these replicons, preferably in a way such that these genes are actively expressed.

The proteins of the present invention are useful in a variety of settings.

Proteins with increased stability and/or resistance to chemical modification, while retaining overall biological activity can be important in industrial applications of enzymes used in unfavorable (harsh) environments, in applications for a large variety of clinical and analytical assays, and in pharmacological applications. Importantly, with respect to therapeutic proteins, the conservative nature of the mutations introduced are not expected to generate new immunogenic properties in the resulting product.

Proteins with decreased stability and/or resistance to chemical modification can be important in a number of applications of proteins in which it is necessary to be able to stop the biological activity of the protein at will or to reduce the half-life of a given therapeutic protein.

Reference is further made to the claims whose contents are also part of this disclosure, as to the different alternatives which form part of this invention.

Procedures according to the invention will now be described by way of examples. It will of course be understood that these examples are representative of how similar modifications can be induced in other biologically active proteins. In these examples, reference is made to the accompanying figures (for abbreviations, see text) in which:

FIG. 1 Heat-inactivation kinetics of metal-free glucose isomerase of EcoAmi(DSM) GI in 50 mM MOPS, pH 7.2 at 25° C. No metal was added.

Figure 2:
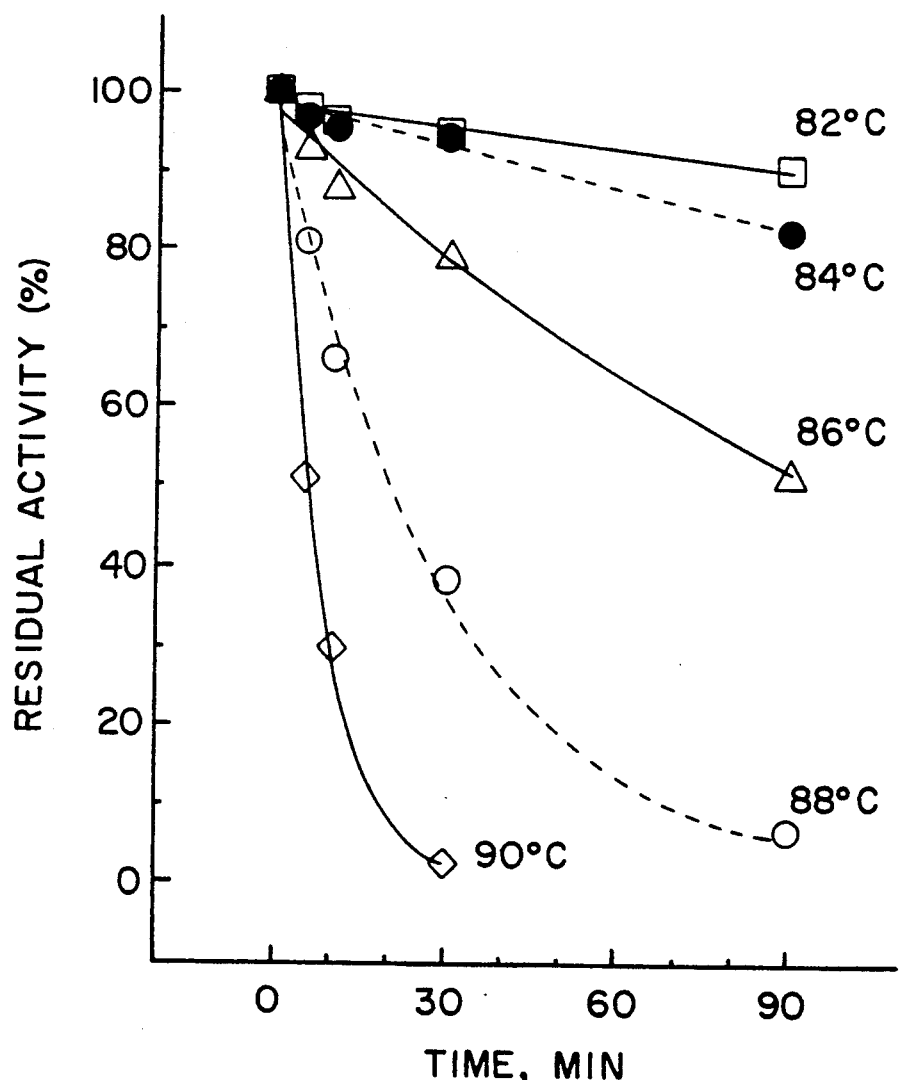

FIG. 2 Same as FIG. 1. 10 mM $Mg^{2+}$ was added.

Figure 3:
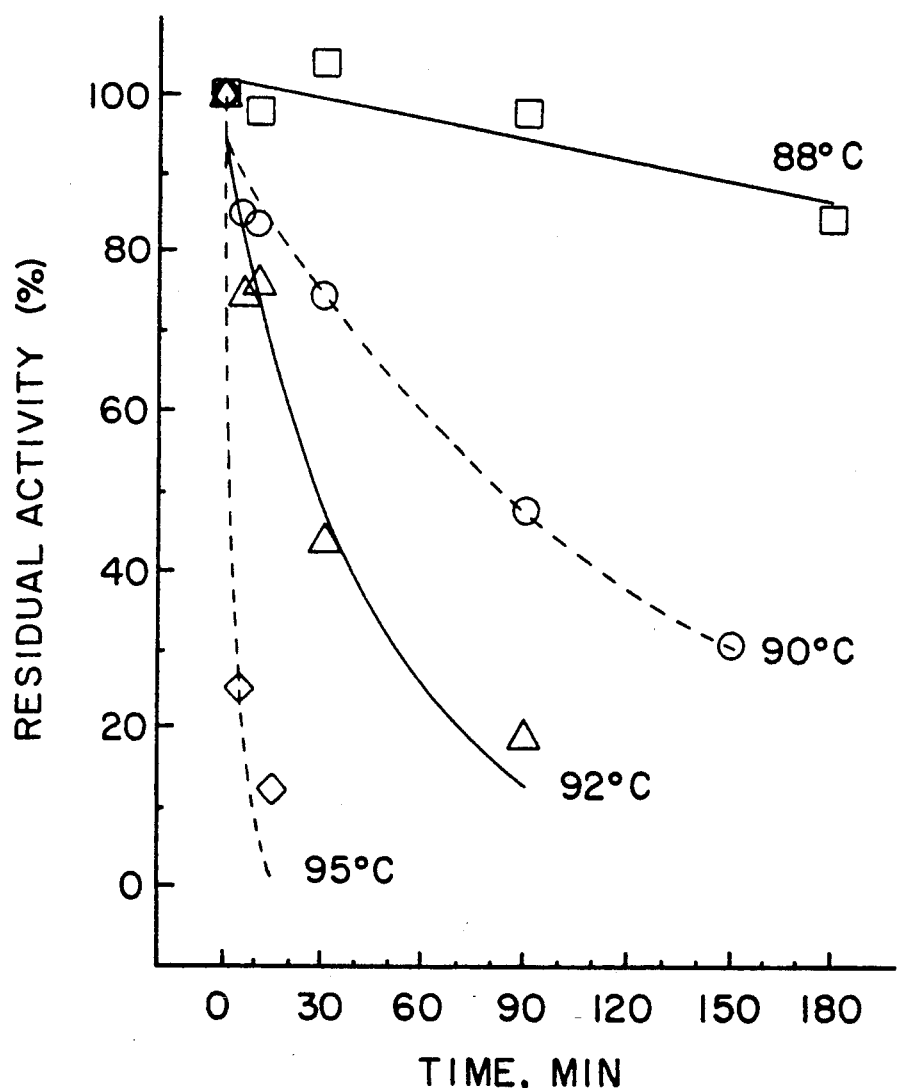

FIG. 3 Same as FIG. 1. 10 mM $Co^{2+}$ was added.

Figure 4:
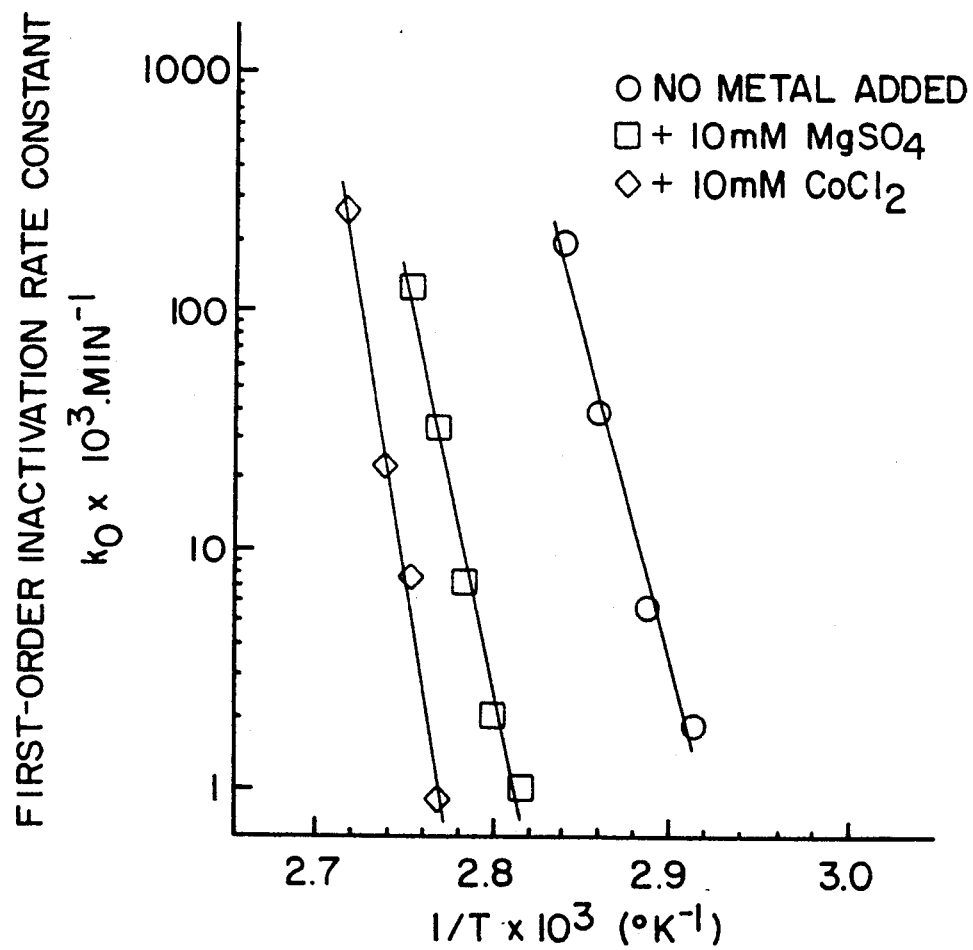

FIG. 4 Arrhenius plot of the temperature dependence for heat inactivation of EcoAmi(DSM) GI in 50 mM MOPS, pH 7.2 at 25° C.

Figure 5:
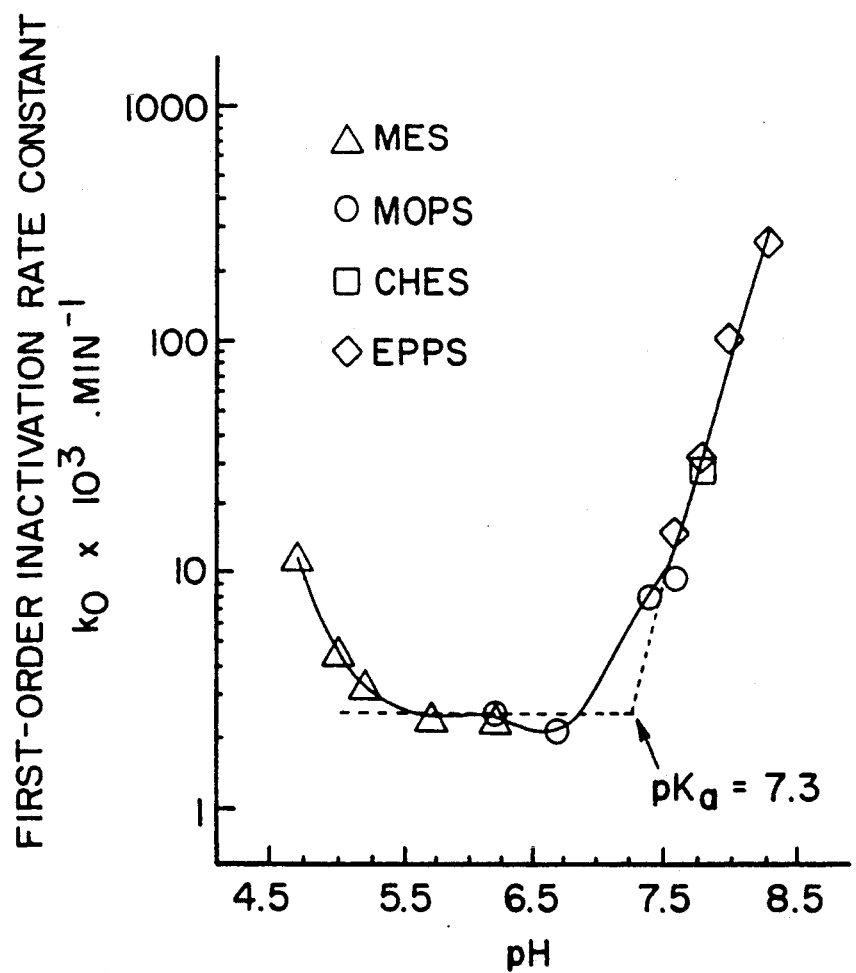

FIG. 5 pH dependence of heat inactivation of metal-free EcoAmi(DSM) GI at 72° C. in the absence of added metal. CHES = 2-(cyclohexylamino) ethane sulfonic acid.

Figure 6:
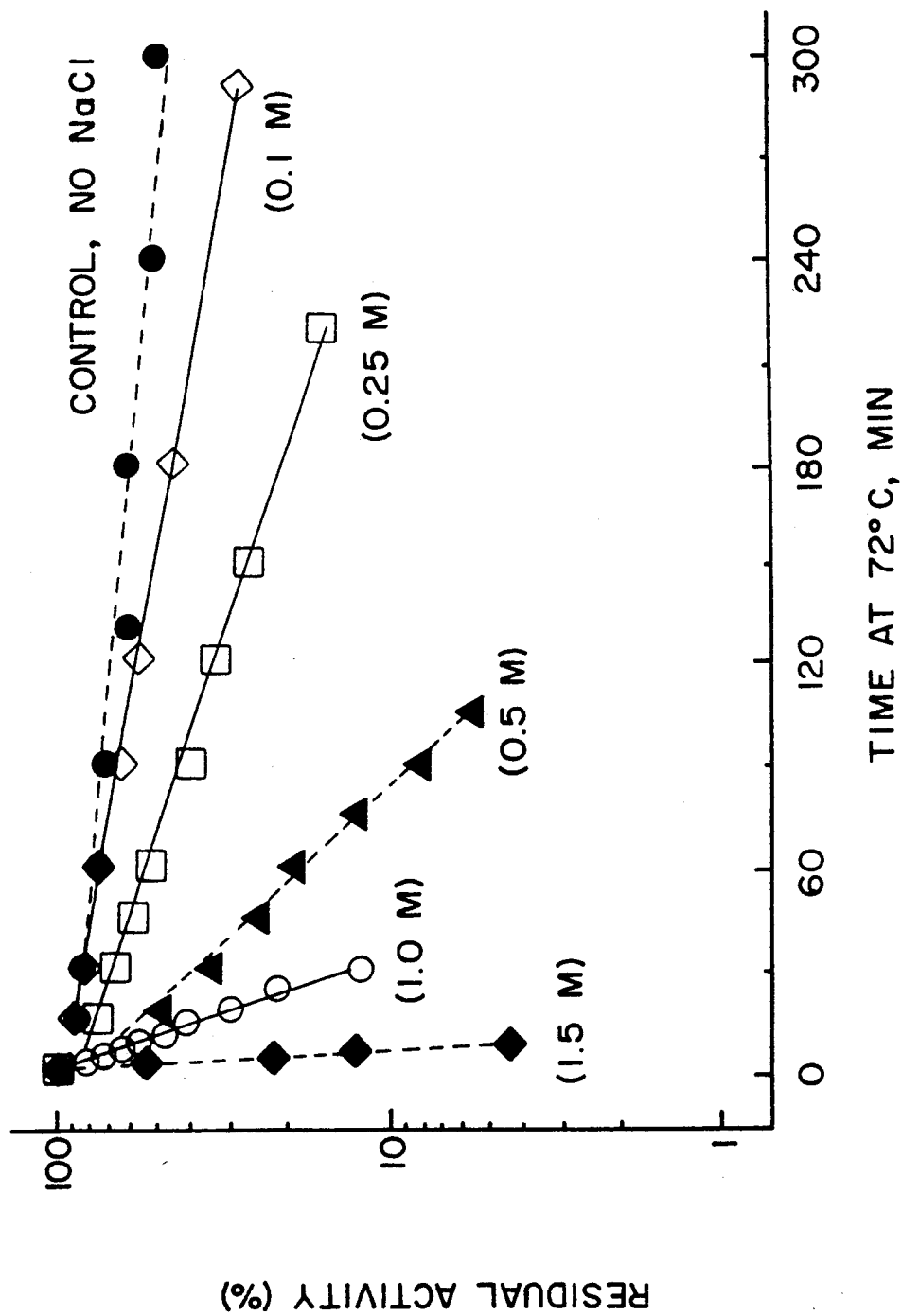

FIG. 6 Ionic-strength effect on the kinetics of heat-inactivation of metal-free EcoAmi(DSM) GI in 50 mM MOPS, pH 6.7, 72° C. No metal added.

FIG. 7 Ionic strength effect on the heat inactivation kinetics of metal-free EcoAmi(DSM) GI in 50 mM MOPS, pH 7.6, 72° C. No metal added.

Figure 8A:
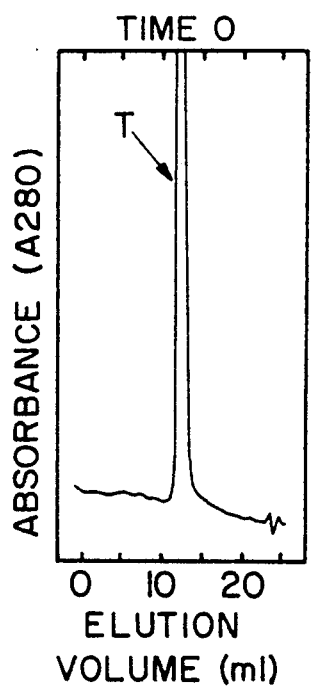
Figure 8B:
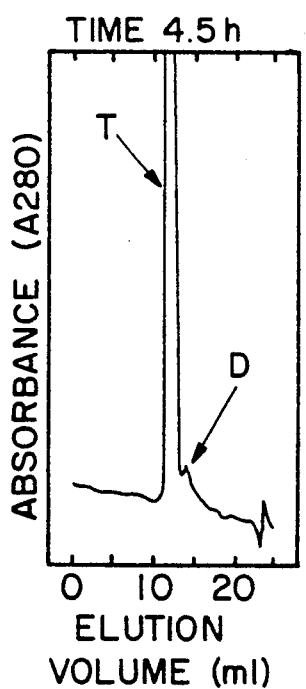
Figure 8C:
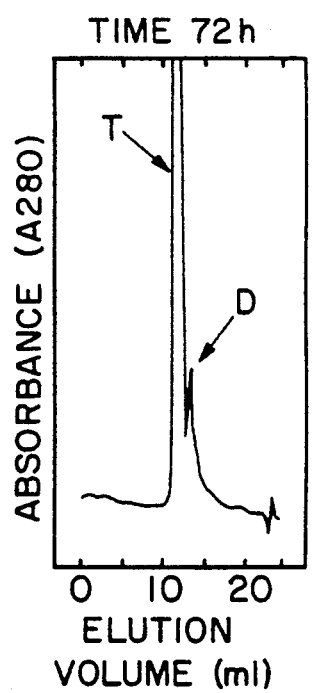

FIGS. 8a-c SEC-HPLC of EcoAmi(DSM) GI after prolonged incubation in 7 M urea at 25 = C.

FIG. 9 A SEC-HPLC of EcoAmi(DSM) GI pretreated with cyanate at 25° C. in the absence of urea. Elution buffer was 50 mM Tris/HCl, pH 8.0, 150 mM NaCl, 0.02% $NaN_3$.

FIG. 9 B Native PAGE of EcoAmi(DSM) GI treated with cyanate at 25° C. in the absence of urea.

FIG. 10 A SEC-HPLC of EcoAmi(DSM) GI pretreated with cyanate in the presence of 5M urea at 25° C.

FIG. 10 B Native PAGE of EcoAmi(DSM) GI treated with cyanate at 25° C. in the absence of urea.

FIG. 10 A SEC-HPLC of EcoAmi (DSM) GI pretreated with cyanate in the presence of 5M urea at 25° C.

FIG. 10 B Native PAGE of EcoAmi(DSM) GI treated with cyanate in the presence of 5M urea at 25° C.

Figure 11A:
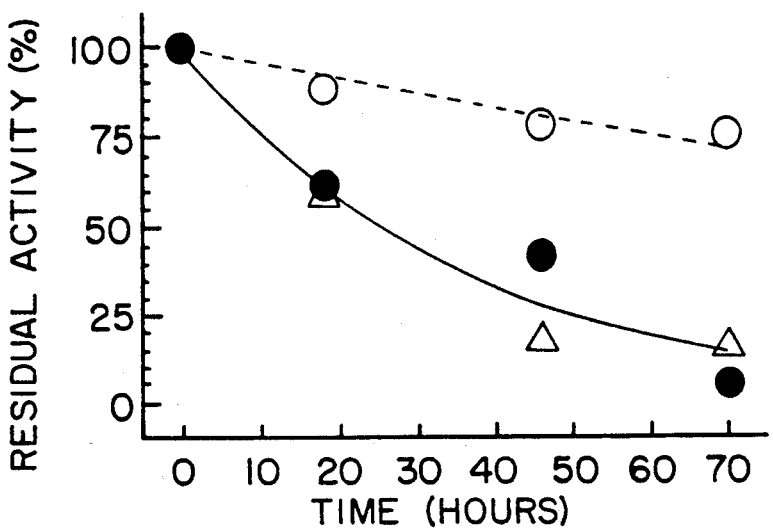
Figure 11B:
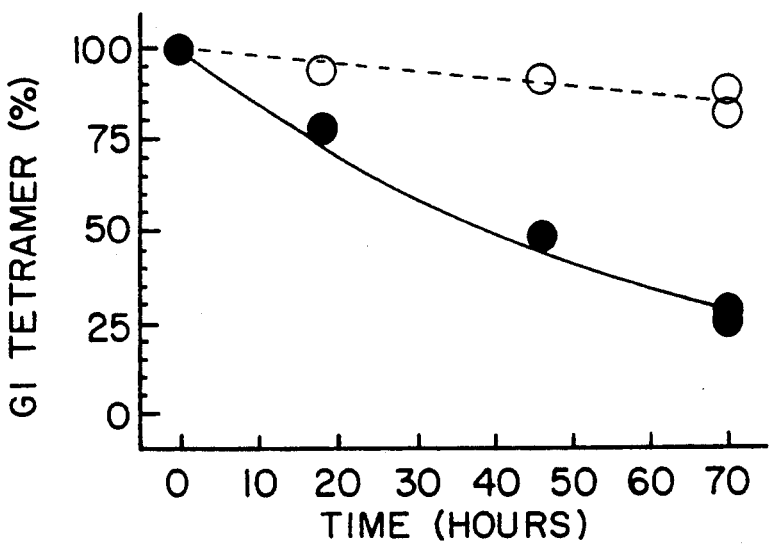
Figure 11C:
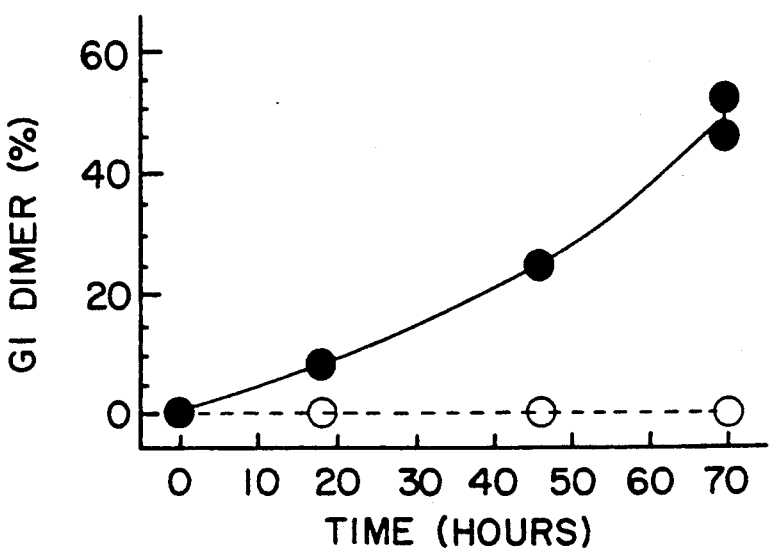
Figure 12A:
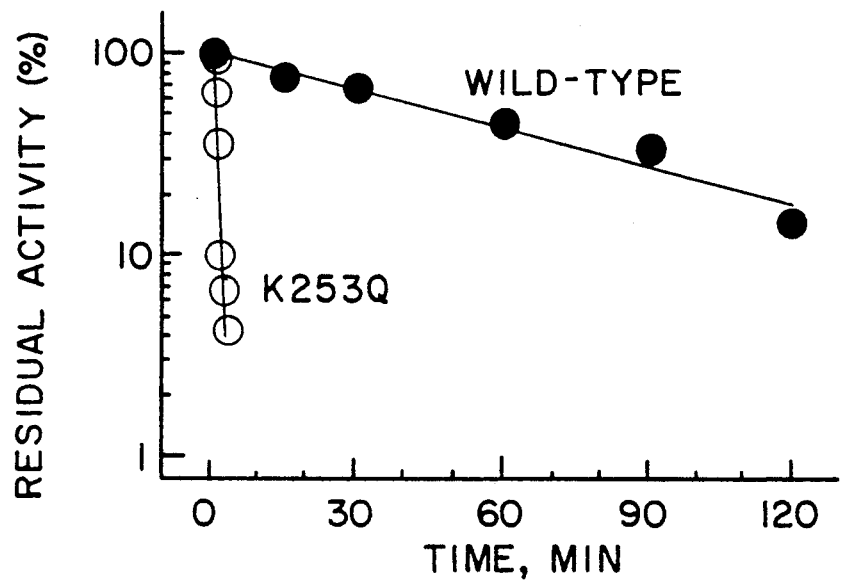
Figure 12B:
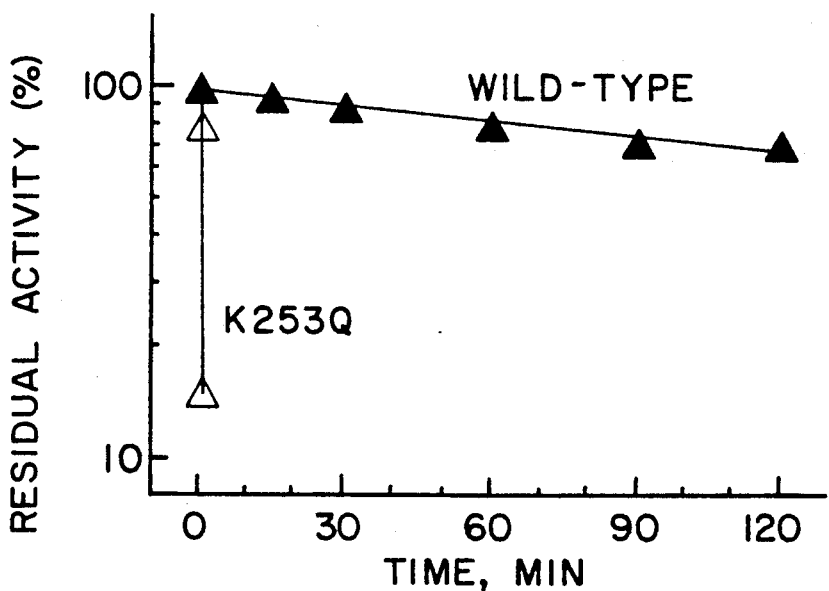

FIGS. 11a-c Glycation of EcoAmi(DSM) GI in 50 mM MOPS, 7.7, 60° C. Open circles: No glucose added; Closed circles: +250 mM glucose; Triangles: Incubation with glucose (250 mM) was followed by extensive dialysis to test for reversibility FIGS. 12a-c Heat-inactivation kinetics of EcoAmi(DSM) GI-mutant K253Q.

Figure 13A:
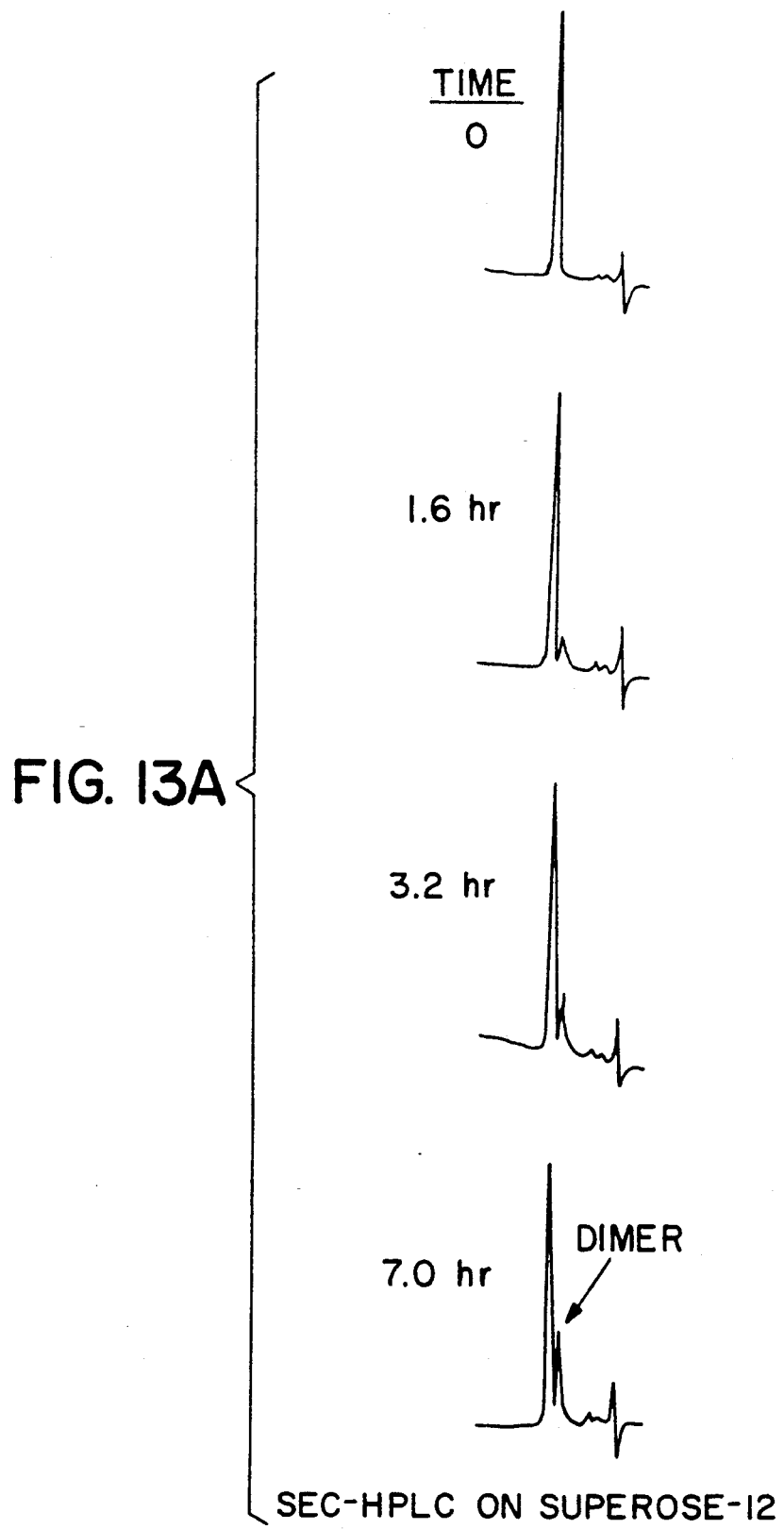
Figure 13B:
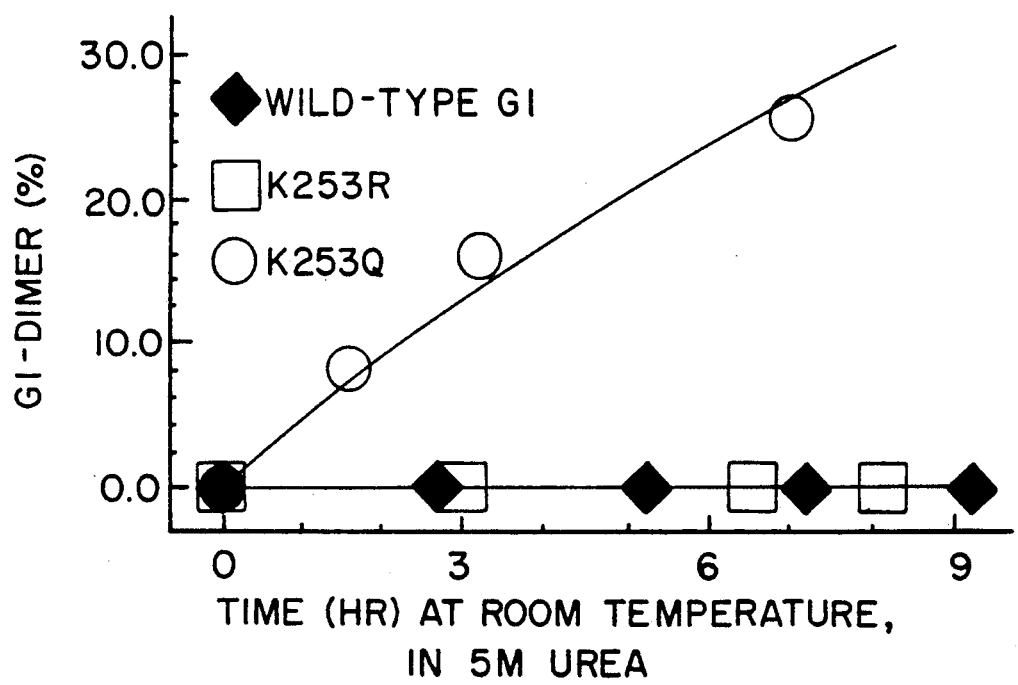

FIG. 13 A SEC-HPLC analysis of the tetramer-dimer dissociation of EcoAmi(DSM) GI-K253Q. B Kinetics of the urea-induced tetramer-dimer dissociation at 25° C. of wild-type EcoAmi(DSM) GI and GI mutants K253R and K253Q.

Figure 14:
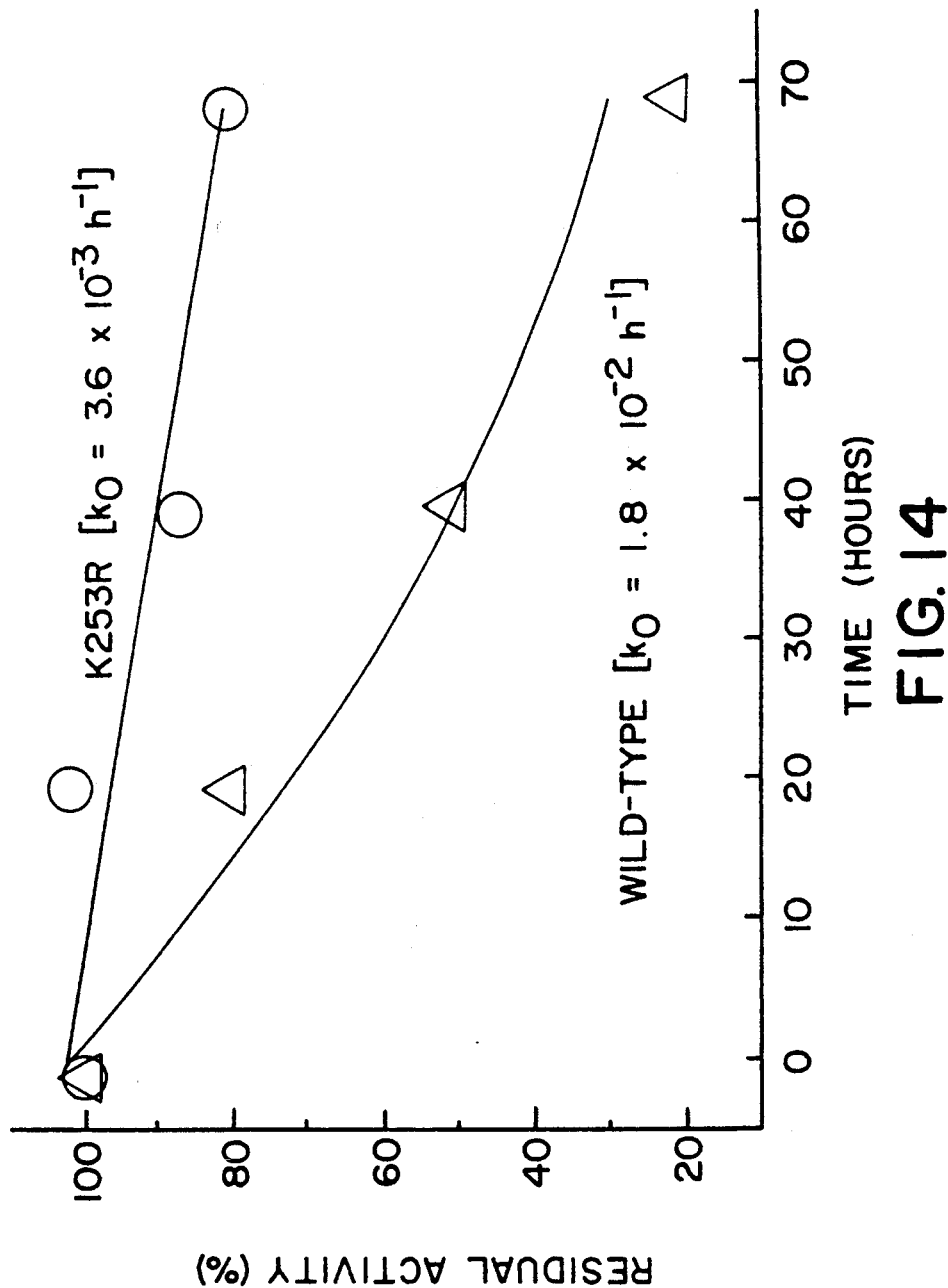

FIG. 14 Kinetics of the glycation-induced inactivation of EcoAmi(DSM) GI mutant K253R at 60° C. in 12.5 mM Potassium phosphate, pH 7.7.

FIG. 15a-c Nucleotide and amino acid sequence of EcoAmi(DSM) GI.

FIG. 16a-c Complete nucleotide sequence of the $P_R$-gi transcriptional unit as comprised as a EcoRI-XbaI fragment in pMa5-GI and pMc5-GI. The arrows above the sequence indicate the beginning and the end of Actinoplanes missouriensis DNA and the start and stop codons of gi are similarly indicated.

FIGS. 17a-b Nucleotide sequence of the tac-sod hybrid gene. Lysine residues that were changed to arginines are boxed. Unique restriction sites used for preparation of the gapped strands are indicated.

FIG. 18 Alignement of the amino acid sequences of the human and bovine CuZnSOD

Figure 19A:
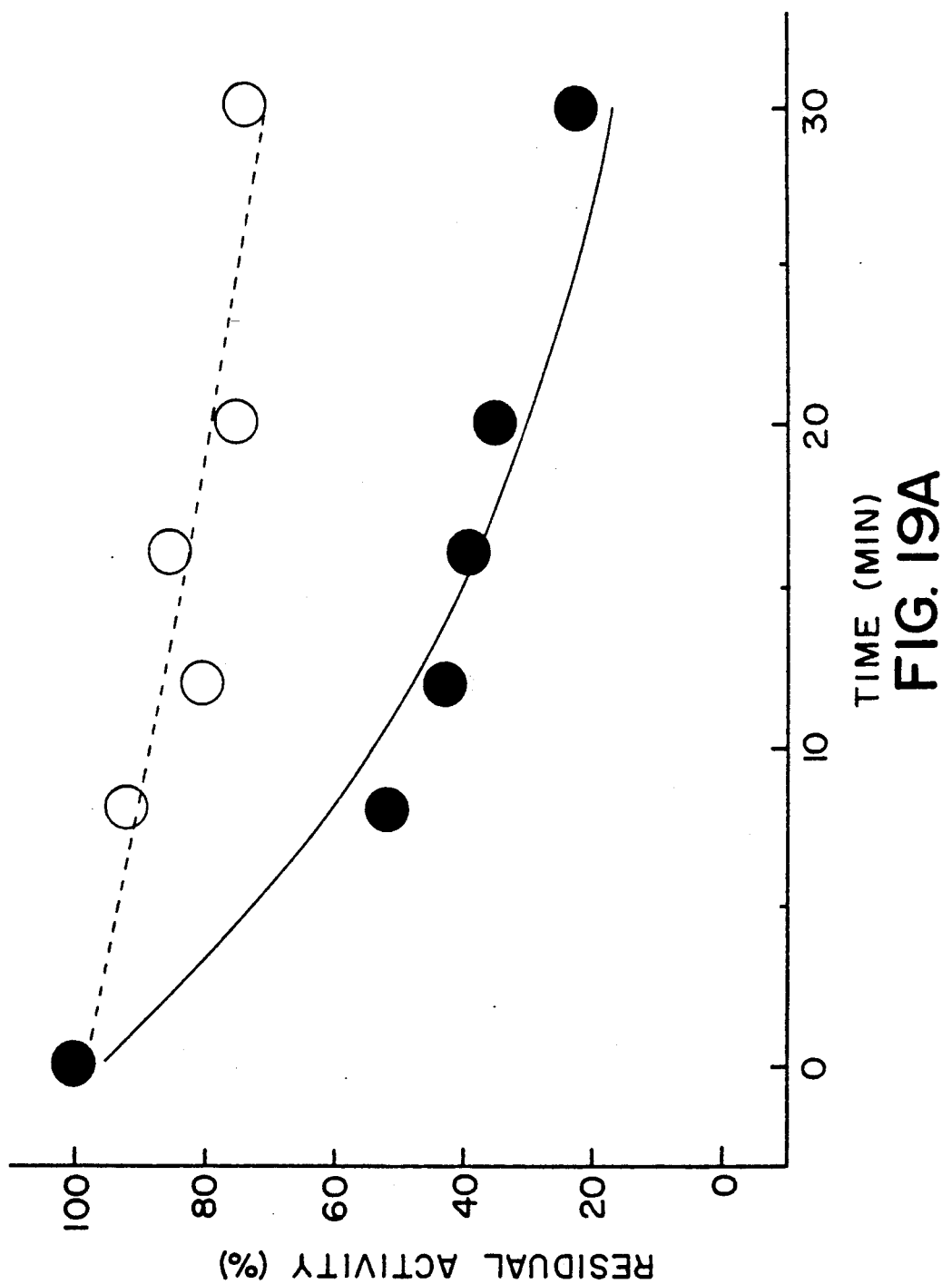
Figure 19B:
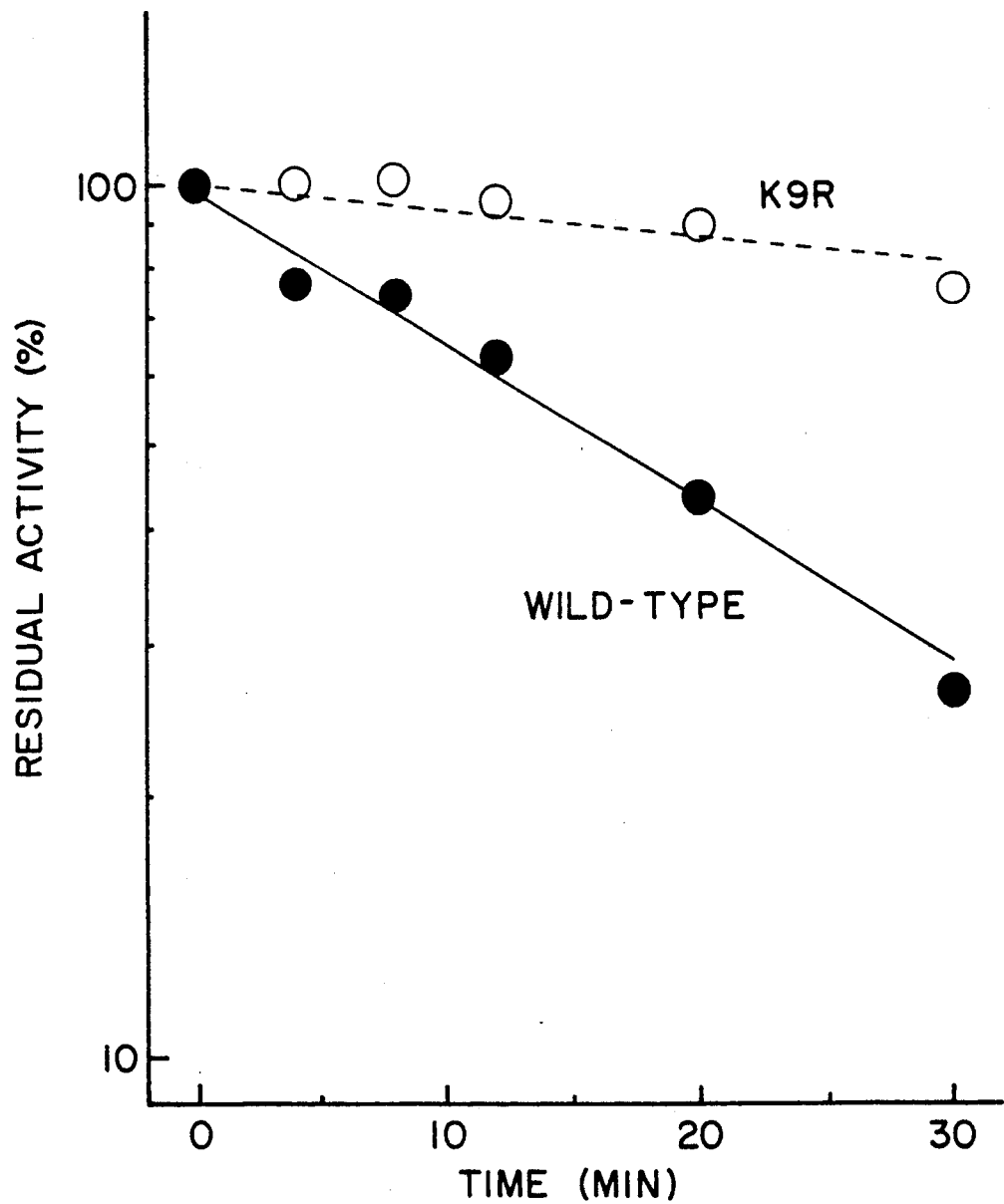

FIG. 19 A Heat-inactivation kinetics of CuZnSOD-WT (closed circles) and CuZnSOD-K9R (open circles): CuZnSOD (0.2 mg/ml; produced by E.coli WK6) was incubated at 85° C. in 20 mM potassium phosphate, pH 7.8, for the indicated time intervals. Heat-inactivation was stopped by cooling the samples to 0° C. for 10 min before adding 50–100 volumes of 0.1 mg/ml catalase in 52.7 mM TCDA buffer. Aliquots of 0.050 ml (100–200 ng/ml, final CuZnSOD concentration) were used for the pyrogallol enzymatic assay as described in the text. Specific activities were 5,000 units/mg for CuZnSOD-WT and 5,200 units/mg for CuZnSODK9R.

B Heat-inactivation kinetics of CuZnSOD-WT (closed circles) and CuZnSOD-K9R (open circles): CuZnSOD (0.2 mg/ml) was incubated for 18 h at 4° C. in 20 mM potassium phosphate, pH 7.8, containing 0.025 mM $CuSO_4$ and 0.025 mM $ZnSO_4$, and then at 85° C. Aliquots were withdrawn at appropriate times and processed as indicated in the legend to FIG. 1. The data represent the mean of duplicate determinations using both 100 and 200 ng CuZnSOD in the final assay mixture.

FIGS. 20a-d Nucleotide sequence of the tac-gap expression module inserted between the EcoRI and XbaI sites of pMa/c5-gap1. The BamHI/DraI junction between fragment containing the tac promoter and the gap gene is indicated by an arrow.

The derived amino acid sequence of the GAPDH protein is also shown. The glycine 282 residue is boxed. The unique ClaI and StyI sites, used for the preparation of the gapped strand are also indicated.

FIG. 21 Alignement of the amino acid sequences of the Bacillus subtilis (Bsu) and the Bacillus stearothermophilus (Bst) GAPDH.

Figure 22:
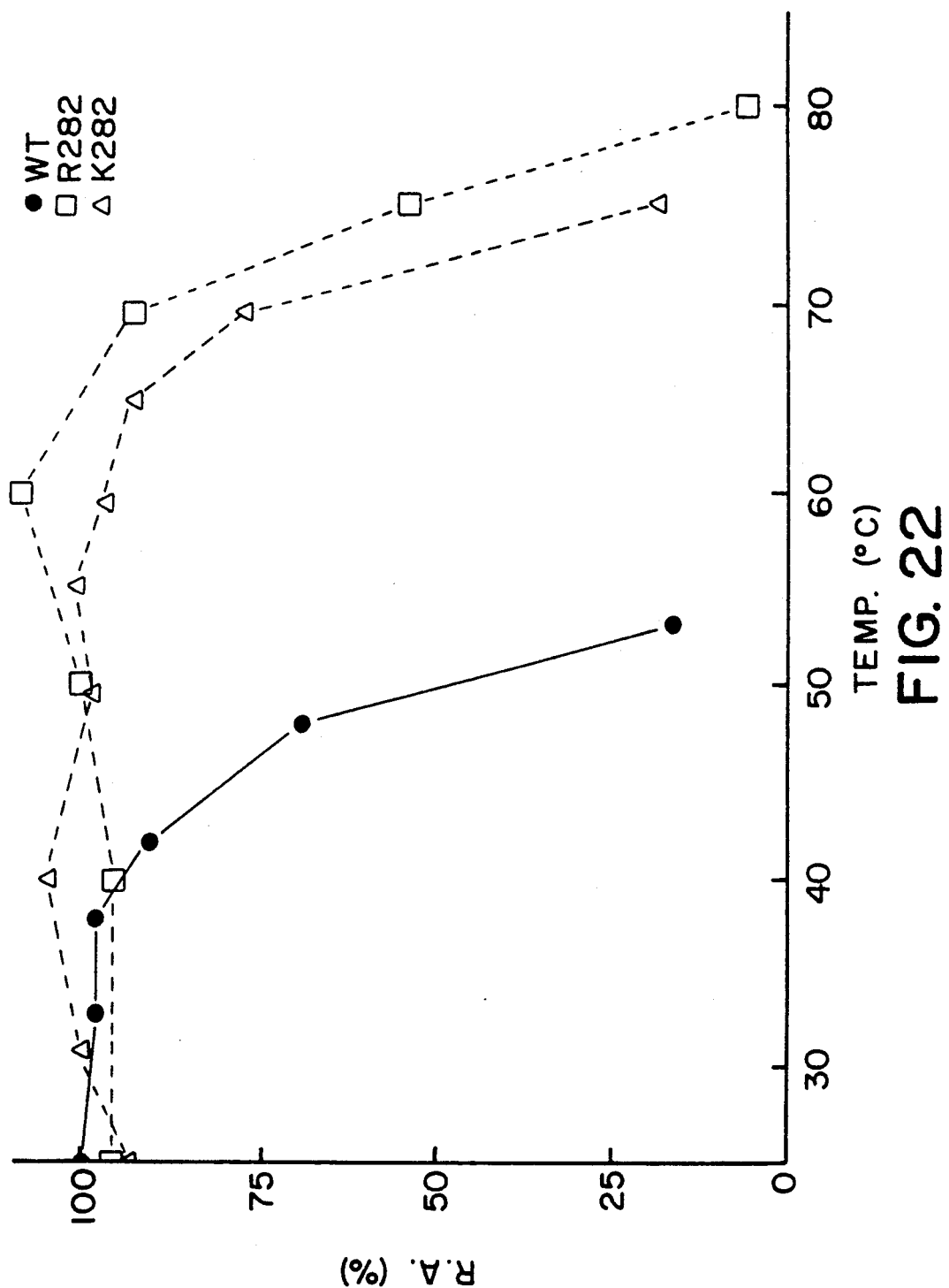

FIG. 22 Residual activity of GAPDH-WT, GAPDH-G282R and GAPDH-G282K after 15-minute incubation at different temperatures.

Figure 23:
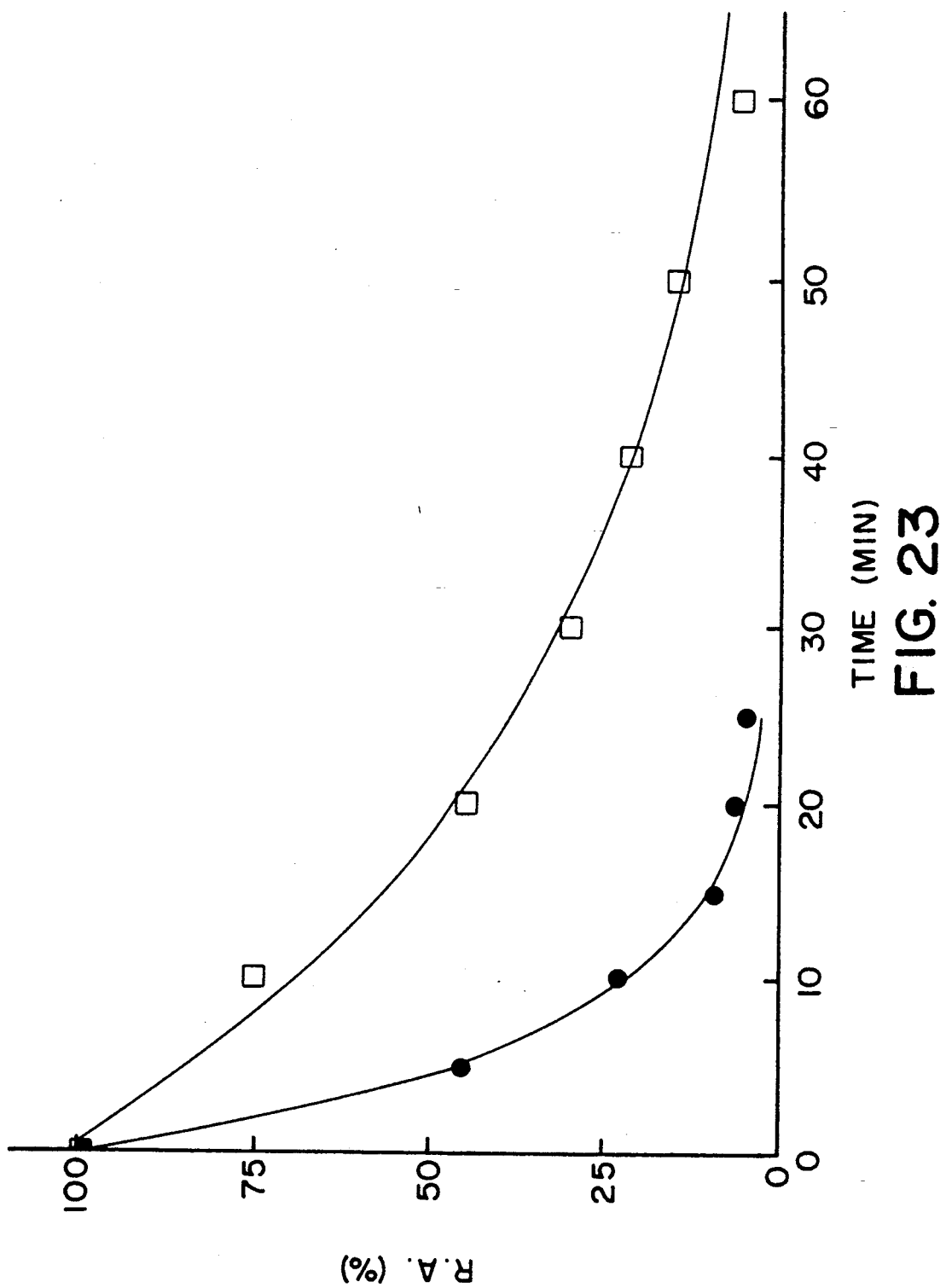

FIG. 23 Heat-inactivation kinetics of GAPDH-G282R (squares) and GAPDH-G282K (circles) at 74.5° C. in the presence of 1 mM $NAD^+$.

Analysis and modeling of 3D-structures of proteins was carried out using the BRUGEL package.

Site directed mutagenesis was performed by the gapped duplex DNA method using the pMa/c plasmid vectors (Stanssens et al., 1987). Mutagenic oligonucleotides were prepared according to the phosphoamidite method (Beaucage and Caruthers, 1981) on an Applied Biosystems 380A DNA synthesizer.

Unless otherwise specified in the examples, all procedures for making and manipulating recombinant DNA were carried out by the standardized procedures described by Maniatis et al. (1982).

The following plasmids, vectors and bacterial strains used or prepared in the Examples have been deposited in the Deutsche Sammlung für Mikroorganismen, Göttingen, West Germany, under the provisions of the Budapest Treaty:

pMc5-8 DSM 4566
pMa5-8 DSM 4567
pEcoR251 DSM 4711

Example 1: Mutant of glucose isomerase from Actinoplanes missouriensis (DSM 43046) with increased thermostability and increased resistance towards chemical modification D-glucose isomerase (GI) is synonymously used for D-xylose isomerase (D-xylose ketol-isomerase, EC 5.3.1.5), an enzyme that converts D-xylose into D-xylulose. The D-glucose isomerase from *Actinoplanes missouriensis* produced by engineered *E.coli* strains is designated as EcoAmi(DSM) GI. To distinguish the *Actinoplanes missouriensis* gene coding for GI from the analogous *E.coli* xylA gene, the former will be designated as gi.

1.A. Isolation and cloning of the GI gene

Total DNA from *Actinoplanes missouriensis* DSM 43046 partially digested with Sau3A. The digest was fractionated on a sucrose gradient and fragments with lengths between 2 and 7 kilobases (kb) were ligated in the unique BglII site of plasmid pECOR251. The xylose isomerase deficient *E.coli* strain AB1886 —as described in Howard-Flanders et al. (1966) and derived from *E.coli* strain AB 1157 (DSM 1563)— was transformed with the ligation mix and subsequently grown on minimal agar plates (Miller, 1972) supplemented with 100 mg/l ampicillin and 0.2% (w/v) xylose (MMX). Thirty seven clones were recovered (designated pAMI1-37) and grown in LB medium containing 100 mg/l ampicillin. Recombinant plasmid DNA was isolated and analyzed by restriction digests. Two groups of plasmid could be recognized, one (e.g. pAMI7) containing a 2.8 kb insert, the other (e.g. pAMI25) containing an 4.0 kb insert. An extensive restriction analysis showed that both types of inserts had a region of about 2.0 kb in common. Sequence determination of this region by the chemical degradation method (Maxam and Gilbert, 1980) revealed an open reading frame with a length of 1182 nucleotides which was identified as the coding region of GI. The nucleotide sequence of gi, together with the derived amino acid sequence are shown in FIG. 15. In the following, the numbering of amino acids refer to FIG. 15.

Very high expression of gi could be achieved in *E.coli* by placing the gene under the transcriptional control of the rightward promoter ($P_{TM}$) of bacteriophage lambda as follows: Plasmid pLK94 (Botterman and Zabeau, 1987) was first modified to eliminate the PstI site in the —lactamase gene. This was done by isolating the 880 bp EcoRI/PstI fragment of pLK70-70p (Botterman and Zabeau, 1987) containing the N-terminal part of the —lactamase gene, and the 1700 base pair (bp) EcoRI/PstI fragment of pLK94 containing the C-terminal part of the —lactamase gene as well as the replication origin. Subsequent ligation of these fragments yielded pLK94p.

pAMI7 was cleaved with PstI and a mixture of two purified fragments of about 1800 bp in length, one of which contains the GI gene, were ligated into the PstI site of pLK94p. The ligation mixture was used to transform *E.coli* strain AB 1886. Ampicillin resistant, GI-transformants were obtained by growing on MMX.

Plasmid DNA was isolated from a few selected transformants and characterized by restriction analysis. Plasmid pLK94p harboring the PstI fragment containing gi was designated as pLK94GI. The orientation of gi is such that the unique BamHI site is located about 470 bp upstream from the GTG initiation codon.

pLK70-70p was cleaved with PstI, made blunt end by the Klenow fragment of DNA polymerase I (Klenow) and subsequently digested with XbaI.

pLK94GI was linearized with BamHI and digested with exonuclease Ba131. Samples were taken at various times -the reaction was stopped with disodium ethylenediaminetetraacetate (EDTA)-, cleaved with XbaI and analyzed by gel electrophoresis to determine the average size of the resected BamHI-XbaI fragments. Fragments, ranging in size from 1350 to 1450 bp were eluted from the gel. The fragments were ligated in pLK70-70p. *E.coli* K514 (Colson et al., 1965) was transformed with the ligation mixture and ampicillin resistant transformants were selected at 37° C. The plasmid DNA, isolated from several transformants was characterized by restriction analysis. Twenty four clones containing plasmids with an intact gi were retained and tested for production of EcoAmi(DSM) GI. Cultures were grown overnight at 37° C. whereafter total cellular extracts were fractionated by polyacrylamide gel electrophoresis (PAGE) on 12.5% sodium-dodecyl sulphate (SDS) (Laemmli, 1970). When compared to an untransformed K514 control culture, one of the clones was found to direct high-level synthesis of a new protein of molecular weight 42 kilodaltons (kd) on SDS-PAGE which was identified as EcoAmi(DSM) GI by Western blotting using a polyclonal serum raised against purified *Actinoplanes missouriensis* GI. The plasmid conferring high EcoAmi(DSM) GI production on *E.coli* K514 was designated as pLK70GI.

The $P_R$-gi transcriptional unit could be excised as a EcoRI-XbaI fragment, the sequence of which is given in FIG. 16. After elution from an agarose gel, this fragment was ligated in both pMa5-8 and pMc5-8 which were digested with EcoRI and XbaI, yielding pMa5-GI and pMc5-GI respectively. These vectors were found to direct equal and efficient synthesis of EcoAmi(DSM) GI while the expression level did not differ significantly from that obtained with pLK70GI.

Expression of gi could be further increased by changing the GTG initiation codon into an ATG triplet. This was done by site directed mutagenesis as described in Example 1.D using the following oligonucleotide primer:

b 5'-GGACAGACATGGTTACC-3'

Wild-type and mutant GI enzymes were produced in *E. coli* strain K514 grown in a medium composed of 1% tryptone, 1% NaCl, 0.5% yeast extract, and either ampicillin (100 mg/l) for pMA type vector or chloramphenicol (25 mg/l) for pMC type vector. Cells were grown overnight at 37° C. and centrifuged. The EcoAmi(DSM) GI enzyme could be purified as follows. The cell pellet was resuspended in a minimal volume of 0.05 M Tris(hydroxymethyl)aminomethane (Tris/HCl), 0.1 mM $CoCl_2$, 10 mM $MgCl_2$, 0.2 M KCl, 5% glycerol, and 5 mM EDTA, pH 8.0, and lysozyme was added to a final concentration of 1.0 mg/ml. After standing for 20 min at 0=C, the cells were lysed using a French press, centrifuged (30 min at 23,000 g), and the supernatant diluted with an equal volume of 5% streptomycin sulphate. Incubation was maintained for 3 hours at 4° C. and followed by centrifugation (30 min at 23,000 g). The resulting supernatant was heated to 70° C. (except for the mutants K253Q and K100R which were heated to only 50° C.) for 30 min and centrifuged again. The soluble upper phase was made 80% with ammonium sulphate. The precipitate which contained most of the enzymatic activity was collected by centrifugation, and then dissolved in 0.02 M Tris/HCl, 5 mM EDTA, 0.85 M ammonium sulphate. The subsequent chromatographic steps included Phenyl-Superose, Sephacryl S-200 HR, and finally Mono-Q HR 10/10. Importantly, the addition of 5 mM EDTA to all buffers for chromatography was necessary in order to eliminate metal ions. Prior to use, the resulting enzyme was dialyzed 3-times against 200 volumes of 10 mM triethanolamine, pH 7.2, containing 10 mM EDTA (final pH is about 5.2), and again against 200 volumes of 5 mM {2-(N-Morpholino)ethanesulfonic acid} (MES), pH 6.0, with 3 buffer changes. The metal content of the final enzyme preparation was determined by atomic absorption spectrometry on a Varian SpectrAA 30/40, and revealed that EcoAmi(DSM) GI was metal free; as an example, it could thus be shown that cobalt ions, which bind to the enzyme with very high affinity, accounted for only $\sim 1 \times 10^{-4}$ mol. per mol. of EcoAmi(DSM) GI monomer (when EDTA was omitted in the chromatographic buffers, the latter value increased to 0.5 mol. cobalt per mol. enzyme monomer). The purity of the EcoAmi(DSM) GI was assessed by SDS-PAGE and silver staining, and also by reversed phase high performance liquid chromatography (HPLC) on a Vydac C4 column.

The enzymatic activity of glucose isomerase was assayed as described below (1 unit of enzymatic activity produces 1.0 micromole of product -D-xylulose or D-fructose- per minute; therefore, specific activity -spa- is expressed as units per mg of GI enzyme).

GI activity could be assayed directly by measuring the increase in absorbance at 278 nm of xylulose produced at 35° C. by isomerisation of xylose by glucose isomerases. This assay was performed in 50 mM triethanolamine buffer, pH 7.5, containing 10 mM MgSO$_4$, and 0.1 M xylose. Glucose isomerase final concentration in the assay was about 0.01 mg/ml, and precisely determined, prior to dilution in the enzymatic assay mixture, by absorption spectroscopy using an extinction coefficient of 1.08 at 278 nm for a solution of enzyme of 1.0 mg/ml.

In the D-Sorbitol Dehydrogenase Coupled Assay, enzymatic determination of D-xylulose was performed at 35° C. as previously described (Kersters-Hilderson et al., 1987) in 50 mM triethanolamine, pH 7.5, 10 mM MgSO$_4$, and 0.1 M xylose, in the presence of $\sim 2 \times 10^{-8}$ M D-sorbitol dehydrogenase (L-iditol NAD oxidoreductase, EC 1.1.1.14), and 0.15 mM NADH, except that the incubation buffer also included 1 mM ethylenebis(oxyethylenenitrilo)tetraacetic acid (EGTA). Glucose isomerase final concentration in this assay was about $2.5 \times 10^{-3}$ mg/ml, and precisely determined as described above.

With glucose as a substrate, GI activity can be assayed by measuring the amount of D-fructose produced during the isomerization reaction using the cysteine-carbazole method which is based on the reaction of ketosugars with carbazole in acids to yield a purple product (Dische and Borenfreund, 1951).

Visualisation of D-xylose isomerases on electrophoretic gels employed the triphenyltetrazoliumchloride (TTC) assay as previously described (yamanaka, 1971). This staining method is based on the reaction of sugars with the tetrazolium salt to form an insoluble formazan at room temperature; the reaction is specific for ketose at room temperature as aldose reacts only at 100° C. On gels, active xylose isomerase can thus be identified as a pink-red band. With minor modifications, this activity test was adapted for use in the Pharmacia PhastSystem. Briefly, following electrophoresis, the native-PAGE gel was transferred to the PhastSystem staining chamber and incubated for 15 min at 50° C. in 20 mM Tris/Hcl, pH 7.2, with 50 mM xylose, 10 mM MgCl$_2$, 0.1 mM CoCl$_2$; after washing with demineralized water 0.5 min at 4° C., the gel was immersed for 3 min at 20° C. in 0.1% triphenyl-tetrazoliumchloride freshly prepared in 1N NaOH; the reaction was stopped by incubating the gel in 2N HCl for 15 min at 20° C.; final wash was in water (0.5 min at 4° C.).

1.B. Kinetics of heat-inactivation of EcoAmi(DSM) GI

Heat-inactivation kinetics experiments were performed on the metal-free glucose isomerase with the additions described in each specific case. In brief, the purified enzyme was equilibrated in the desired buffer and the solution was drawn up into a Hamilton gas-tight syringe with a Teflon needle, that had been previously inserted into a glass mantle connected to a circulating waterbath (Lauda, RM6) set at the indicated temperature. Previous experiments have shown that temperature equilibration of the enzyme solution from 25 to 85° C. is achieved in less than one minute. At appropriate times, aliquots were withdrawn into Eppendorf tubes and the heat denaturation process was quenched by cooling the samples to 0° C.

Alternatively, large samples were incubated as individual aliquots in Reacti-Vials (Pierce).

All buffers were Chelex-treated (Chelex-100, Biorad) to eliminate metal contamination, where appropriate.

1.B.1. Temperature and metal dependence

The kinetics of heat-inactivation of EcoAmi(DSM) GI in 50 mM {3-(N-Morpholino)-propanesulfonic acid} (MOPS), pH 7.2 at 25° C. (pK$_a$=7.15 at 25° C.; dH/° C. = −0.011), as a function of temperature is illustrated in FIG. 1 (No metal added), FIG. 2 (+10 mM MgSO$_4$), and FIG. 3 (+10 mM CoCl$_2$). All the data points are remarkably well fitted by theoretical decay curves corresponding to a first-order process regardless of the temperature used and of the presence or nature of the metal ion.

The data also demonstrate the stabilizing effect of magnesium and, even more so, of cobalt ions. Enzyme inactivation by heat was found irreversible; accordingly, heating was shown to induce protein aggregation. In the presence of Mg$^{2+}$, we could demonstrate that loss of enzymatic activity correlated remarkably well with the extent of protein precipitation.

FIG. 4 summarizes the data of FIGS. 1, 2, and 3, and shows that, in the temperature interval from 60°-95° C., the Arrhenius plots are linear whether metal is present or not.

These results indicate that thermal denaturation of EcoAmi(DSM) GI originates from one single event under all conditions tested; it is not known whether the same limiting step prevails in the absence and in the presence of metal, but the linearity of the Arrhenius plots supports the contention that this step is unique under a specific set of experimental conditions.

1.B.2. pH and ionic strength dependence

The affinity of GI for stabilizing metals is strongly pH dependent; in particular, it is considerably reduced below pH 6. Consequently, the influence of pH on the thermostability of EcoAmi(DSM) GI was studied using the metal-free enzyme in the absence of added metals.

In the pH range from 4.7 to 8.3, the inactivation of EcoAmi(DSM) GI at 72° C. always followed first-order kinetics. FIG. 5 shows that the inactivation rate constant, $k_D$, remained practically unaltered between pH 5.5 and 6.7, but was increased on either side of this pH range.

FIG. 6 demonstrates that the kinetics of heat-inactivation of the enzyme in the absence of added metal was increased as a function of the ionic strength. This, together with the pH dependence data, strongly indicates that polar residues are involved in the thermal stability of EcoAmi(DSM) GI.

This contention is further supported by the data in FIG. 7 where it is shown that a moderate increase in pH (i.e. pH 6.7 to pH 7.6 at 72=C) significantly amplified the destabilizing effect of sodium chloride.

1.B.3. Effects of urea and cyanate

GI is a tetramer made of four identical subunits (Rey et al., 1988).

The influence of urea was assessed in an attempt to identify structural changes that might account for the loss of enzymatic activity as a result of heating i.e. subunit dissociation and/or unfolding.

The oligomerization state of the enzyme was analyzed by size-exclusion high performance liquid chromatography (SEC-HPLC) on Superose-12 at room temperature, using an elution buffer consisting of 50 mM Tris/HCl, pH 8.0 at 25° C., and 150 mM NaCl, following prolonged incubation of the enzyme in 7M urea at room temperature. Native GI elutes as a tetramer on SEC-HPLC. FIG. 8 shows that prolonged incubation in urea is necessary to induce a dissociation of the native EcoAmi(DSM) GI-tetramer into dimers.

Since cyanate is known to be generated from urea in solution on standing, it was speculated that chemical modification of the enzyme by cyanate might be responsible for the observed subunit dissociation. To test this hypothesis, the enzyme was incubated for 16 to 24 days at room temperature in 0.2 M borate, pH 8.5, and 150 mM NaCl, containing cyanate concentrations ranging from 0 to 200 mM, and this in the absence or presence of freshly prepared 5.0 M cyanate-freed urea (a freshly prepared stock solution of 10 M urea in Milli-Q water was passed over a column of AG 501-X8 (D) resin (Bio-Rad) according to the recommendations of the manufacturer; this treatment eliminates ionic contaminants among which cyanate).

Figure 9B:
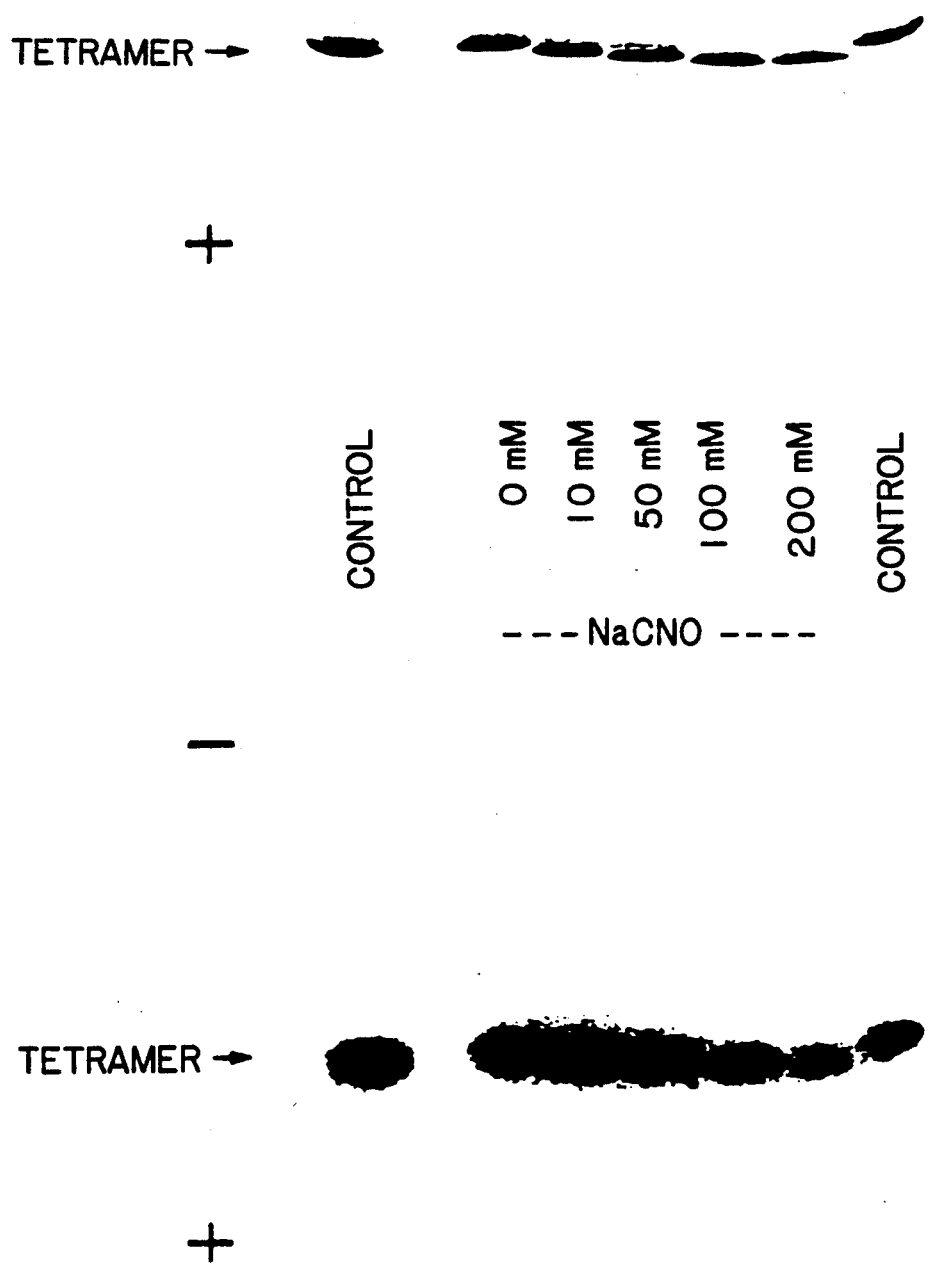
Figure 10A:
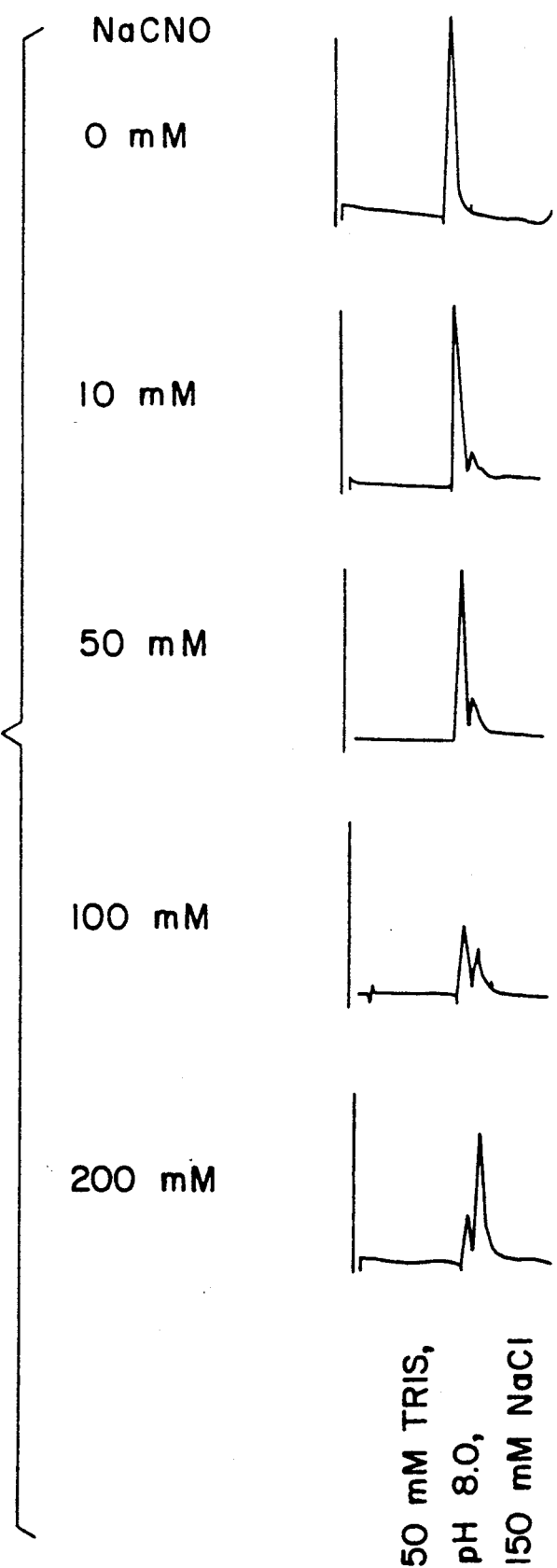

The following observations were made:
1. Treatment with cyanate alone could not alter the elution profile of EcoAmi(DSM) GI on SEC-HPLC (FIG. 9A). Native PAGE did reveal a dose-dependent chemical modification of the enzyme as evidenced by the increase in negative charge (FIG. 9B, upper panel), but without apparent loss of enzymatic activity as shown by TTC-staining of the gel (FIG. 9B, lower panel).
2. After 16 days of incubation of EcoAmi(DSM) GI in 5.0 M cyanate-freed urea, no dimer formation was apparent by SEC-HPLC (FIG. 10A). Some dimer-dimer dissociation, however, was observed on native PAGE (FIG. 10B, upper panel, 0 mM NaCNO) suggesting that at the urea concentration used (5 molar), generated cyanate induced minor chemical modification which, although not directly leading to tetramer dissociation, weakened the dimer-dimer association to an extent that dissociation could be brought forth under the influence of the electrical field applied during PAGE. Alternatively, it can also be proposed that the combined influence of urea and of the electrical field brings about tetramer to dimer dissociation.
3. The simultaneous addition of cyanate to EcoAmi(DSM) GI in 5.0 M urea readily brought about tetramer to dimer dissociation in a concentration-dependent fashion. This was demonstrated both by SEC-HPLC (FIG. 10A) and by native PAGE (FIG. 10B, upper panel). The retardation in PAGE of the dimer after incubation at high cyanate concentrations is likely to result from an increased unfolding of the enzyme under these conditions. On native PAGE, the dimers showed no GI-activity after TTC staining (FIG. 10B, lower panel). This finding suggests that enzymatic activity is lost upon GI-tetramer dissociation into dimers and/or due to chemical modification.

In conclusion, the presence of both cyanate and urea is required to observe EcoAmi(DSM) GI tetramer dissociation into dimers. Since cyanate alone was ineffective, the chemically-modified amino-group(s), which are involved in the stabilization of the tetramer structure of the enzyme, are not solvent-accessible in the absence of urea. Urea probably destabilizes the dimer/dimer interaction, thereby exposing amino acid(s) previously buried within the dimer/dimer interface. These residues, bearing either an alpha and/or an epsilon amino group, become thus available for carbamylation by cyanate. In turn, covalent attachment of cyanate to intersubunit contact residue(s) stabilizes the dimer form of the enzyme. It can therefore be proposed that the dissociation of EcoAmi(DSM) GI tetramers into dimers is probably one of the primary events in thermodenaturation. In support of this hypothesis, it could be observed that higher protein concentrations stabilized the enzyme against denaturation by heat (data not shown).

1.B.4. Glycation

Proteins have been shown to undergo glycation, i.e. nonenzymatic modification of alpha and epsilon amino groups by glucose and numerous other sugars. It was predicted that under application conditions (high glucose concentrations, pH 7.5, and prolonged utilization) glycation of EcoAmi(DSM) GI was likely to occur as well; in particular, if EcoAmi(DSM) GI tetramers dissociate into dimers at high temperature, one would anticipate that the same amino acid residue(s) reacting with cyanate in the presence of urea would become glycated with concomitant tetramer-dimer dissociation, and possibly loss of catalytic activity,.

Metal-free EcoAmi(DSM) GI was incubated in the absence of magnesium at 60° C. without or with D-glucose (250 mM) in 50 mM MOPS, pH 7.7 at 60° C. At appropriate times, aliquots were withdrawn, cooled to 25° C. and tested for residual enzymatic activity by the direct xylulose absorbance assay at 278 nm.

FIG. 11, Panel A, shows that the presence of glucose significantly increased the rate of heat-inactivation of the enzyme at 60° C. This effect was not reversible as extensive buffer exchange against 50 mM MES, pH 6.0, at 4° C., could not restore the catalytic efficiency of EcoAmi(DSM) GI (triangles in FIG. 11, Panel A). Moreover, analysis of the reaction products by SEC-HPLC clearly demonstrated that, as predicted, glycation was accompanied by tetramer to dimer dissociation in a time-dependent fashion (FIG. 11, Panels B and C), a finding that supports he contention that tetramer splitting occurs at high temperature. Dissociated dimers are trapped by covalent modification with glucose of reactive amino groups likely to reside in the interdimer contacts.

FIG. 11, Panel D, shows that heating also caused formation of a protein aggregate; this aggregation was greatly enhanced in the presence of glucose. It is not known, however, whether aggregate formation occurs independently of, or only subsequent to, GI dissociation into dimers. Very similar results could be reproduced in a different buffer system: 12.5 mM potassium phosphate, pH 7.7 at 60° C.

It is interesting to recall that the presence of urea was necessary for cyanate to produce stable GI dimers, whereas glucose exhibits the same properties at high temperature in the absence of urea. Therefore, we can conclude that both urea and heating cause the dissociation of EcoAmi(DSM) GI tetramers into dimers, thereby exposing amino acid residues located in the interdimer interface; previously inaccessible amino groups becomes then available to react with cyanate or glucose, thus trapping the enzyme in the dimer state.

1.C. Identification of lysine residues in the subunit interfaces of glucose isomerase of Actinoplanes missouriensis GI is a tetramer consisting of four identical subunits (A, B, C and D) (Rey et al., 1988) which can be viewed as an assembly of two dimers (AB and CD). One can therefore distinguish two categories of subunit interfaces, interfaces between the monomers within one dimer (intradimer interface) and the interface between two dimers (interdimer interface).

A residue is said to participate in the subunit interface contacts if its accessible surface area (ASA) (Lee and Richards, 1971) calculated in the isolated subunit differs from that determined in the oligomer. Table 2 compiles the ASAs for the 20 subunit lysine residues both in the isolated monomer and in the GI tetramer. Eleven of these residues are seen to participate in subunit interfaces. Only Lys-100 and Lys-253 bury an extensive area ($149A^2$ and $110A^2$, respectively) in the subunit interfaces, and become almost completely buried in the tetramer. In other words, both of these residues have low solvent accessibility in the tetramer. Also, both residues are not implied in the catalytic activity of EcoAmi(DSM) GI. Furthermore, Lys-100 and Lys-253 are involved in electrostatic interactions in the subunit interfaces. Lys-100 in the A-subunit (A_Lys-100) stabilizes, through hydrogen bonding the last turn of a small helix near position 373 in the B-subunit. Lys-253 in the A-subunit (A_Lys-253) on the other hand is involved in ionic interdimer interaction with Asp-190 of the C-subunit. Using model building techniques (as described in Delhaise et al., 1984) it was observed that the environment of Lys-100 is not likely to accommodate a substitution to Arg, whereas the mutation of Lys-253 to Arg would be sterically possible because no bad physical contacts were apparent and ionic interactions with Asp-190 remained favorable.

1.D Amino acid replacements of specific lysine residues in glucose isomerase of Actinoplanes missouriensis According to the present invention, the substitution of Lys-253 with arginine would stabilize the electrostatic interaction across the dimer-dimer interface and thereby increase the stability of EcoAmi(DSM) GI towards thermal inactivation. Moreover, this substitution would also prevent chemical modification (by glucose or cyanate) at position 253.

To assess the importance of electrostatic interactions of the A_Lys-253/C_Asp-190 ion pair in the heat stability of EcoAmi(DSM) GI, Lys-253 was mutated into glutamine to eliminate the ionic character of the lysine side-chain, this mutation being otherwise reasonably conservative.

Site-directed mutagenesis was performed according to the gapped duplex DNA (gdDNA) method using the pMa5-8 and pMc5-8 like phasmid vectors (Stanssens et al. 1987). Since the mutagenesis strategy requires the use of unique restriction sites upstream and downstream of the region to be mutagenized, two additional cleavage sites were introduced in the GI coding sequence without altering the encoded amino acid sequence. A KpnI site was created by nucleotide base-exchange of G at position 177 into A using the following oligonucleotide primer:

5'-CGAAGGGTACCAGG-3'

A XhoI site was created by substitution of a C for a G at position 825 using the following oligonucleotide primer:

5'-GCCGTTCTCGAGGAGGTCG-3'

The conversion of the GTG into an ATG codon (see Example 1.A) and the creation of the KpnI site were accomplished in a single mutagenesis experiment in which the relevant enzymatically phosphorylated oligonucleotides were annealed to a gdDNA derived from single stranded pMc5-GI and the large BamHI-AatII fragment of pMa5-GI.

The XhoI site was introduced in a separate experiment; the gdDNA used was constructed from single stranded pMc5-GI and the large SacI-SmaI fragment of pMa5-GI. The three mutations were assembled in a single gene by combining the appropriate fragments of the double mutant and the XhoI mutant. The resultant triple mutant was designated as pMa5-I. The complementary pMc5-I was constructed by insertion of the small EcoRI-XbaI fragment of pMa5-I, containing the $P_R$-gi hybrid gene, between the EcoRI and XbaI sites of pMc5-8.

pMa5-I and pMc5-I are the basic vectors used for the production of both the wild type and mutant GI's.

In all site-directed mutagenesis experiments, described hereinafter, use was made of a gdDNA prepared from the single stranded form of pMa5-I and a suitable fragment of pMc5-I.

1.D.1. LYSINE-253→GLUTAMINE

For the construction of the gdDNA, the large SacI-XhoI fragment of pMc5-I and the following oligonucleotide primer were used:

5+-CCTGGTCGAACTGCGGGCCG-3'

The mutant enzyme was well expressed; specific activity using xylose as a substrate was 96% that of wild-type EcoAmi(DSM) GI (Table 3).

Heat-inactivation at 72° C. in 50 mM MOPS, pH 7.4 at 72° C., in the absence of metal, obeyed first-order kinetics, and showed that the mutation provoked a 60- fold increase in the denaturation rate constant from $1.4 \times 10^{-2}$ min$^{-1}$ for wild-type to 0.9 min$^{-1}$ for K253Q (FIG. 12, Panel A).

In the presence of 10 mM MgSO$_4$ at 85° C. in 50 mM MOPS, pH 6.5 at 85° C. (FIG. 12, Panel B), the first-order decay rate constant had a value of 1.2 min$^{-1}$ for K253Q, about 350 times higher than that of wild-type enzyme ($k_D = 3.4 \times 10^{-3}$ min$^{-1}$).

Analysis of the oligomeric structure of the K253Q enzyme by size-exclusion chromatography revealed an intact tetramer Prolonged incubation in 5 molar, cyanate-freed, urea in 0.2M borate, pH 8.5, 0.15 M NaCl, however, demonstrated that the K253Q mutant readily dissociated into dimers as shown in FIG. 13, Panel A; FIG. 13, Panel B, summarizes the data showing the progress curve for dimer formation for wild-type and mutant enzymes; dissociation of tetramers into dimers occurs in the heat-labile mutant enzyme but not in the wild-type enzyme.

The experiments described above probe the structural basis of the stability of the EcoAmi(DSM) GI molecule. Specific alteration of residue K253 into glutamine introduces a temperature— and also a urea-sensitive mutation and consequently identifies a locus of essential interactions. A clear correlation is established between the susceptibility of the mutant to heat-inactivation and the extent of tetramer dissociation into dimers promoted by urea at room temperature.

1.D.2. LySINE-253→ARGININE

For the construction of the gdDNA, the large SacI-XhoI fragment of pMc5-I and the following oligonucleotide primer were used:

5'-CCTGGTCGAACCGCGGGCCG-3'

The EcoAmi(DSM) GI mutant, K253R, was well expressed and displayed an enzymatic activity 120% that of wild— type's with xylose as a substrate (Table 3).

The thermostability of this mutant was tested in 50 mM N-2-Hydroxyethylpiperazine-N'-2-ethanesulfonic acid (EPPS), pH 7.5, 5 mM MgSO$_4$, at temperatures ranging from 82°–92° C. Table 4 lists the half-lives in hours for K253R and wild-type enzymes; the results demonstrate that over this temperature range K253R is consistently more stable than wild-type enzyme.

To assess the stability of the mutant K253R with regard to inactivation by glucose at high temperature, both enzymes were incubated in the presence of 250 mM D-glucose at 60° C. in 12.5 mM potassium phosphate buffer, pH 7.7. Shown in FIG. 14 is the time course of inactivation for about 70 hours; the data clearly demonstrate the enhanced protection against inactivating —irreversible— chemical modification achieved in the K253R mutant as its half-life is increased 5-fold compared to wild-type's.

The present invention has thus been used successfully to engineer mutations leading to a more stable GI.

As a negative control, Lys-100 was mutated into arginine, in which case it was expected that, as mentioned earlier, a bad steric accommodation of the new residue would lead to a decrease of stability, although without affecting enzymatic activity.

1.D.3. LySINE-100→ARGININE

For the construction of the gdDNA, the large KpnI-AatII fragment of pMc5-I and the following oligonucleotide primer were used:

5'-CCGCCGTCCCGGAACACCGG-3'

The specific activity of the K100R GI was 22 units per mg using xylose as a substrate. It is thus comparable to the activity of the wild type EcoAmi(DSM) GI (24.5 units per mg). Heat-inactivation of this mutant enzyme, however, proceeded about 100 times faster with $k_D = 0.3$ min$^{-1}$, in 50 mM EPPS, pH 7.5 at 84° C., 5 mM MgSO$_4$.

Example 2: Mutants of human CuZn superoxide dismutase with increased thermostability and increased resistance towards chemical modification Superoxide dismutases (E.C.1.15.1.1) are enzymes that catalyze the conversion of superoxide radicals into hydrogen peroxide according to the following reaction:

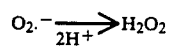

Superoxide radicals are ubiquitously generated in many aerobic biological oxidations (Bannister et al., 1987) either by direct or indirect processes.

CuZnSODs are generally very stable enzymes which have been reported to exist as homodimers; each subunit has a molecular weight of approximately 16,000 daltons, contains one Cu(II) and one Zn(II), and associates with its partner by noncovalent interactions.

Previous studies have indicated that chemical modifications involving amino groups in CuZnSOD is accompanied by a reduction in enzymatic activity. Since the N-terminal amino group is acetylated, the N-epsilon amino group of lysines is the only candidate for such modification. The succinylated bovine enzyme retains only 10% activity, but also spontaneously dissociates into monomers on 0.1% SDS-PAGE (Marmocchi et al., 1982), whereas a major portion of the native protein behaves as a tetramer (Hartz et al., 1972, Marmocchi et al., 1982). Carbamylation by cyanate also produces an enzyme with reduced activity (Cocco .et al., 1982). The human CuZnSOD was similarly found to undergo glycation, i.e. nonenzymatic, covalent attachment of glucose to amino groups, with concomitant inactivation (Arai et al., 1987 a). The glycated sites were subsequently identified as Lys-122 and Lys-128 (Arai et al., 1987 b)

Cloning of the cDNA of human CuZn SOD in *E.coli* has been described by Hallewell et al. (1985) and in European patent application EP 138111. The DNA sequence encoding the CuZnSOD cDNA will be designated as sod.

In accordance with the present invention, several lysine residues could be replaced with arginine so as to produce mutant CuZnSOD enzymes with a higher thermal stability and/or higher stability towards chemical modification.

2.A. Cloning of the cDNA of human CuZnSOD

The sod gene fused to the tac promoter (De Boer et al., 1983) was obtained from *E.coli* strain D1210 harboring plasmid pSOD11 as described in European patent application EP 138111 and deposited with the American Type Culture Collection (ATTC) under accession number 39679.

The DNA fragment comprising the tac-sod hybrid gene was isolated as follows. Plasmid pSOD11 was partially digested with AccI, the restriction fragments were made blunt ended by treatment with Klenow and digested with SalI. The 1260 bp fragment, containing the tac-sod hybrid gene, was ligated to the large fragment of plasmid pMc5-8 which was digested with SmaI and SalI. The ligation mixture was used to transform E.coli WK6 (Zell and Fritz, 1987). Transformants were selected on LB agar plates containing 25 μg/ml chlorampenicol and isolated plasmid DNA was checked by restriction analysis. Plasmids which contained the tac-sod hybrid gene between the EcoRI and SalI sites of pMc5-8 was designated as pMc5sod11. The 1260 bp EcoRI-XbaI of pMc5-sod11 was transferred into the EcoRI and XbaI sites of pMa5-8 yielding plasmid pMa5-sod11.

The integrity of the tac-sod hybrid gene in the pMa/c vectors was checked by sequencing according to Maxam and Gilbert (1980). The sequence of this gene is given in FIG. 17.

To obtain recombinant CuZnSOD, an overnight culture of E.coli WK6 —or alternatively a sodAsodB— strain of E.coli which is devoid of endogenous SOD activity (Carlioz and Touati, 1986)—, containing pMa5-sod11 (resp. pMc5-sod11) was diluted 100-fold in TB medium (1.2% Bacto-tryptone, 2.4% Bacto-yeast extract, 0.5 % glycerol, 28 mM $KH_2PO_4$, 72 mM $K_2HPO_4$) supplemented with 100 ppm $CuSO_4$, 0.46 ppm $ZnSO_4$ and 0.1 mg/ml ampicillin. The cells were grown shaking at 30=C to a density of $OD_{650 nm}=0.4$, at which time expression of the sod gene was induced by the addition of IPTG (isopropyl-β-D-thiogalactopyranoside; 0.25 mM final concentration). Cell density reached from 15 to 25 OD as measured by absorbance at 600 nm. Cells were harvested after an induction period of 16 hours, washed with PBS, and then frozen and thawed. After centrifugation, the cell pellet was resuspended in a minimal volume of 20 mM Tris/HCl, 5% glycerol, pH 8.0, to achieve an $OD_{600}$ of 200/ml.

Under these conditions, both clones, i.e. E.coli WK6 (pMa5-sod1) and WK6 (pMc5-sod1) direct the efficient synthesis of a soluble 16 kD protein as apparent from the analysis of total cellular extracts, prepared by sonication, on SDS-12.5% polyacrylamide gels (Laemmli, 1970). When compared to an uninduced control culture, the SDS-PAGE protein profiles of induced cultures contain an additional 16 kD band.

The 16 kD protein was present in the soluble fraction in which it was estimated to amount to about 5–7 % of total protein content in E.coli WK6 (pMa5-sod1) and 10–15% in the E.coli sodAsodB- (pMa5-sod1) strain. Purification was performed as follows. Lysozyme (0.5 mg/ml, final) was added to the cell suspension, then made 0.1 mM EDTA. After incubation for 20 min on ice, the cells were lysed using a French Press, and the resulting homogenate was clarified by centrifugation. Streptomycin sulphate (0.5 %) was added to the supernatant, and after 3 hours at 4° C., the insoluble material was removed by centrifugation. The resulting supernatant was then made 0.05 mM $ZnSO_4$ and 0.1 mM $CuSO_4$, and incubated 2–4hours at 25° C., before being heated to 70° C. for 30 min. After elimination of the insoluble material by centrifugation, the clarified lysate was dialyzed twice against 50 volumes of 10 mM Tris/HCl, pH 8.0, at 4° C., and chromatographed onto Q-sepharose Fast Flow by means of a gradient from 40 to 200 mM $CH_3COONa$ in 20 mM Tris/HCl, pH 8.0. The SOD containing fractions, as assessed by SDS-PAGE, and by native PAGE with Coomassie staining and with activity staining (Beauchamp and Fridovich, 1971), were pooled. At this stage, the CuZnSOD produced in E.coli sodAsodB⁻was already highly pure as assessed by SDS-PAGE. The latter enzyme was further dialyzed twice against 50 volumes of 10 mM potassium phosphate, pH 7.8, and used as such. For the enzyme produced by the E.coli WK6 strain, the SOD pool, originating from the Q-sepharose, was made 1.4 M ammonium sulphate and chromatographed onto a Pharmacia Phenyl-Superose HR 10/10 column equilibrated in 20 mM Tris/HCl, 1.4 M $(NH_4)_2SO_4$, pH 8.0. Under these conditions, the CuZnSOD was not bound to the hydrophobic resin, in contrast to an E.coli endogenous protein contaminant which eluted only when the ammonium sulphate concentration had been reduced to about 0.7 M. The void peak from the Phenyl-Superose, which contained the CuZnSOD, was dialyzed at 4=C against 50 volumes of 10 mM Tris/HCl, pH 8.0, with two buffer changes. The enzyme was then concentrated on a Mono-Q HR 5/10 run in 20 mM Tris/HCl, pH 8.0, including 2 μM $CuSO_4$ and $ZnSO_4$, and eluted with a gradient from 0 to 160 mM NaOAc. The resulting enzyme was finally dialyzed against two buffer changes of 10 mM potassium phosphate, pH 7.8, and was shown to be free of contaminant by SDS-PAGE. It could be shown that no SOD activity from endogenous E.coli SODs remained in the samples.

CuZnSOD could be assayed by the nitroblue tetrazolium (NBT) assay as modified from Winterbourn et al. (1975). The assay was performed in Microtiter-plates. The assay mixture contained 50 mM potassium phosphate, pH 7.8, 50 micromolar NBT (Janssen), 0.1 mM EDTA, 0.03% Triton-X 100, and various amounts of CuZnSOD. The reaction was started by addition of 2 mM riboflavin-5'-phosphate (Bio-Rad) to the microtiter-plate set onto a fluorescent light-box. The plate was covered with aluminium foil, incubated for 12 minutes, and the absorbance at 540 nm was determined with a Titertek Multiskan MCC plate reader.

The pyrogallol assay was essentially as described by Marklund and Marklund (1974) with minor modifications. Briefly, The CuZnSOD inhibition of pyrogallol autooxidation was performed in an assay mixture containing 0.90 ml of 52.7 mM Tris/cacodylic acid, 1.1 mM diethylenetriamine pentaacetic acid, pH 8.20 (TCDA buffer), and 0.050 ml of various concentrations of CuZnSOD in 52.7 mM TCDA buffer containing 0.05 mg/ml catalase (from Aspergillus niger; Merck). Following incubation at 25° C. for 10 min, the mixture was vortexed at very high speed to achieve air equilibration, immediately before starting the reaction by addition of 0.050 ml of 4.0 mM pyrogallol (Merck) in 1 mM cacodylic acid (Serva) (the stock solution of pyrogallol in 1 mM cacodylic acid was stable for at least 1 day at 4° C.). The increase in absorbance at 420 nm as a function of time, which measures the rate of autooxidation of pyrogallol, was determined at 25° C. over a period of 6 min during which linearity was observed. The inhibition of pyrogallol autooxidation as a function of added CuZnSOD was found to be linear up to a concentration of 250–300 ng/ml of enzyme.

SOD activity on acrylamide gels could be visualized using the assay described by Beauchamp and Fridovich (1971) as adapted for use with Pharmacia PhastGels in the Phastsystem staining chamber. Following electrophoresis, the gel was soaked at 50° C. first in 2.5 mM NBT for 20 min, and then in 36 mM potassium phosphate, pH 7.8, containing 28 mM TEMED (Bio-Rad), 28 micromolar riboflavin-5'-phosphate (Bio-Rad), and 0.1 mM EDTA, for an additional 30 min. The gel was then illuminated using a fluorescent light-box till enough contrast was obtained (~15-20 min), and subsequently fixed by soaking for 30 min in 10% ethanol, 5% acetic acid. The gel could be preserved by immersing it for 30 min in 10% acetic acid, 15% glycerol, before drying it.

Protein concentration was determined using the Bradford assay with bovine serum albumin as a standard.

2.B. Identification of residues

The human CuZnSOD exhibits about 80% homology with the bovine (Bos taurus) enzyme (FIG. 18), the 3D-structure of which has been solved to high resolution (Brookhaven data base pdb file pdb2sod —Tainer et al., 1982). Accordingly, the structure of the human CuZnSOD can be derived using the bovine CuZnSOD as a template (Hallewell et al., 1989).

Examination of the bovine CuZnSOD crystal structure shows that Lys-9 is a potential candidate for mutation into arginine for the purpose of improving the thermostability of the enzyme.

Examination of the human CuZnSOD indicated that Lys-122 and Lys-128 (corresponding to Lys-120 and Arg-126, respectively, in the bovine CuZnSOD), which are implicated in glycation (Arai et al., 1987 b), are fully solvent accessible, and due to charge conservation, their replacement by arginine should be well accommodated in the CuZnSOD structure. Therefore, Lys-122 and Lys-128 were mutated into arginine to prevent chemical modification and resulting inactivation as produced by glucose.

The structure of the human CuZnSOD could be derived from that of the bovine CuZnSOD as follows: One model (Model I) was obtained by substitution of all residues, differing from the human CuZnSOD and having one or more atoms within a radius of 10 Angstrom of Lys-9 in the O-subunit, with their corresponding residues in the human CuZnSOD. No additions or deletions were required. The following substitutions had to be performed: O_Thr-17>Ile, O_Thr-34>Lys, O_Gln-53>Ala, O_Met-115>Leu, O_Lys-9>Lys (the arrow denotes the substitution event e.g. O_Thr-34>Lys means that Lys is substituted for Thr at position 34 in the O chain).

Another model (Model II) was obtained by substitution of all residues, differing from the human CuZnSOD and having one or more atoms within a radius of 10 Angstrom from either Lys-120 or Arg-126 in the O-subunit, with their corresponding residues in the human CuZnSOD. No additions or deletions were required. The following substitutions had to be performed: O_Asp-40>Leu, O_Pro-121>Ala, O_Arg-126>Lys.

For each of the two models, the substitutions were carried out at full atomic detail in the absence of water molecules and in the order as they appear in the above lists. Main chain atoms were taken from the bovine CuZnSOD template. Side chain orientations were determined by exhaustive map computation varying each of the side chain dihedral angles in steps of 30 in the 0-360 interval and by selecting the configuration with the lowest energy. The O_Lys-9>Lys substitution was also done with an energy map, simulating the corresponding human CuZnSOD conformation. Following these substitutions, the crystal water molecules were added to the CuZnSOD structure and the model was subjected to 500 steps of conjugated gradient energy minimization, restraining all heavy atoms except those of the introduced side chains. For convenience the human numbering will be used.

In Model I, Lys-9 residue was changed into an Arg, while in Model II, Lys-122, or alternatively Lys-128, was changed into an arginine. For each of these substitutions, the same procedure as outlined above was followed.

Analysis of the environments of the three lysine residues as well as those of the three arginine mutations indicated that all these residues are fully exposed to solvent and are sterically accommodated (Table 5; negative non bonded energies).

According to this invention, it can be expected that mutation of these residues to arginine will lead to improved thermostability. From Table 5, it can be seen that in SOD-K9R the 010-014 loop region of the protein is stabilized and that Arg-9, when compared to Lys-9 in SOD-WT, is involved in more numerous and generally stronger hydrogen bonds.

The stability of the K128R mutant will additionally be increased by the formation of one hydrogen bond (see Table 5) which is not present in the human CuZn-SOD.

The stability of the K122R mutant on the other hand will additionally be increased by the formation of two hydrogen bonds (see Table 5) which are not present in the human CuZnSOD.

It can also be expected that substitution of Lys-122 and Lys-128 with arginines will abolish chemical modifications undergone by the N-epsilon amino group of Lys.

2.C. Site-Directed mutagenesis

The replacement of the lysine residues at positions 9, 122, and/or 128 with arginines, made use of gapped DNA molecules which were constructed as follows:

for K9R mutation : from the single stranded pMc5-sod1, the large EcoRI-StuI fragment from pMa5-sod1 and the following oligonucleotide:

5'-CCGTCACCCCTCAAAACAC-3' for the K122R mutation : from the single stranded pMc5-sod1, the large StuI-StyI fragment from pMa5-sod1 and the following oligonucleotide:

5'-GTCATCTGCTCTTTCATGAACCACC-3' for the K128R mutation: from the single stranded pMc5-sod1, the large StuI-StyI fragment from pMa5-sod1 and the following oligonucleotide:

5'-CATTTCCACCGCGGCCCAAGTC-3'

The double mutant SOD-K122R/K128R was produced by appropriate mutagenesis of either one of the single mutants.

2.D. Evaluation of the thermostability of the K9R mutant of human CuZnSOD.

The rates of inactivation of SOD-WT and SOD-K9R were determined at a fixed temperature. Thus, following incubation of SOD in 20 mM potassium phosphate, pH 7.8 at 85° C. in both the absence and presence of metal, aliquots were withdrawn at appropriate time intervals and cooled to 0=C. Residual enzymatic activity, as measured using the pyrogallol assay at 25° C., is shown in FIG. 19.

The decay obeyed first-order kinetics. The inactivation rate constant at 85° C. for SOD-WT in the absence (respectively, presence) of metal was 0.06 min$^{-1}$ (0.04 min$^{-1}$) which corresponds to a half-life of 12 min (17 min). The rate constant for heat-inactivation at 85° C. for SOD-K9R was 0.01 min$^{-1}$ (0.007 min$^{-1}$), so that the half-life increased to 65 min (98 min).

2.E. Evaluation of the human CuZnSOD-K122R/K128R.

To evaluate the protective effect of the Lys to Arg mutations against glycation for the CuZnSOD-K122R/K128R double mutant, both wild-type and mutant enzymes (1 mg/ml; 7,000 units/mg) were incubated at 60° C. in 0.2 M potassium phosphate, pH 7.35, in the absence or presence of 0.1 M α-D-glucose. At appropriate times, aliquots were withdrawn, immediately cooled to 0° C., and diluted 500-fold with a stock solution of 52.7 mM TCDA, containing 1 mg/ml catalase, and enzymatic activity was measured using the pyrogallol assay.

It is clear from the data in Table 7 that considerable protection against glycation-induced inactivation is realized by replacing Lys-122 and Lys-128 with arginines.

Moreover, even in the absence of glucose, the stability of CuZnSOD-K122R/K128R at 60° C. is markedly higher than that of CuZnSOD-WT.

The bovine CuZnSOD is engineered so as to include arginines at positions 9 and 120. The resulting enzymes are more stable than the wild-type bovine CuZnSOD.

The present invention has thus been used successfully to engineer mutations leading to more stable CuZn-SODs.

Example 3 Mutants of glyceraldehyde-3-phosphate dehydrogenase (GAPDH) from Bacillus subtilis with increased thermostability Glyceraldehyde-3-phosphate dehydrogenase (GAPDH-E.C. 1.2.1.12) is a homotetrameric enzyme which catalyzes the following reversible reaction in glycolysis,:

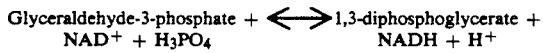

Glyceraldehyde-3-phosphate + NAD$^+$ + H$_3$PO$_4$ $\rightleftharpoons$ 1,3-diphosphoglycerate + NADH + H$^+$ The 3D structure of GAPDH from *Bacillus stearothermophilus* (Bst) (Skarzynski et al., 1987) and from lobster (Moras et al., 1975; Biesecker et al., 1977) have been determined. These two GAPDH's differ considerably in their thermostability, Bst GAPDH being much more stable than lobster GAPDH. The difference in thermostability between these two enzymes has been suggested to originate from the presence of intersubunit bridges in the Bst GAPDH which are absent in the lobster enzyme (Biesecker et al., 1977; Skarzynski et al., 1987). However, comparisons with other thermostable (e.g. from *Thermus aquaticus*) and thermolabile GAPDH's (e.g. pig, yeast) have revealed that no single factor is responsible for thermostabilization of this enzyme Thus, differences in the extent of hydrophobic interactions, intersubunit hydrogen bonds and ion pairs, as well as differences in surface residues have all been implicated to explain thermostability differences (Walker et al., 1980, Argos, 1989).

The gene coding for GAPDH in *Bacillus subtilis* strain BR151 (young et al., 1969; Bacillus Genetic Stock Center N 1A40) (Bsu) has been cloned and sequenced (Viaene et al., 1988; Viaene and Dhaese, 1989). This gene will be denoted as gap.

The GAPDH from Bsu turned out to be very unstable. To increase the thermostability of this enzyme and in accordance with the present invention, we have introduced salt bridges across the subunit interfaces by site-directed mutagenesis of the Gly282 residue into Lys-282 or Arg-282 — the two mutants will be denoted as GAPDH-G282K and GAPDH-G282R respectively. It could be expected that any one of these changes would drastically increase thermostability with respect to the wild-type GAPDH (GAPDH-WT); moreover, it can be expected that GAPDH-G282R would be more thermostable than GAPDH-G282K.

3.A. Isolation and cloning of Bacillus subtilis GAPDH

The isolated recombinant plasmid, pBSgap-1 (Viaene et al., 1988) was obtained from P.Dhaese (Rijksuniversiteit Gent, Belgium). The plasmid consists of a partial Sau3A fragment containing the entire gap coding region, inserted in the BamHI site of pUC18 (Yannisch-Perron et al., , 1985).

High level production of Bsu GAPDH in *E.coli* was obtained by putting the gap gene under the transcriptional control of the hybrid trp-lac (i.e. "tac") promoter (De Boer et al., 1983). The expression vector construct was obtained by ligating the following three DNA fragments:

a) the tac promoter which was obtained as follows. Plasmid pMT416 (Hartley, 1988) was digested with BamHI. The protruding 5'-ends were made blunt-ended by treatment with Klenow. Finally, the DNA was digested with EcoRI. The small (+/−107 bp) fragment, containing the tac promoter was isolated from gel. The orientation of the tac promoter on this fragment is such that transcription proceeds towards the BamHI site.

b) the large gel-purified EcoRI-XbaI fragment of pMc5-8 c) the 1255 bp DraI-XbaI fragment of pBSgap-1 containing the gap coding region. This fragment was also eluted from gel. The DraI cleavage site is located 16 nucleotides upstream from the ATG initiation codon; the XbaI site is located in the pUC18 poly-restriction-site linker.

The ligation mixture was used to transform *E.coli* WK6 (Zell and Fritz, 1987) selecting on LB agar plates containing 25 μg/ml chloramphenicol. Plasmid DNA was isolated from a few selected transformants and characterized by restriction analysis. The plasmid with the desired structure, i.e. the tac-gap hybrid transcription unit inserted between the EcoRI and XbaI sites of pMc5-8, was identified and designated pMc5-gap1. The sequence of the tac-gap hybrid gene is shown in FIG. 20. For purposes of mutagenesis, a pMa type version of this vector was constructed by transferring the EcoRI- XbaI tac-gap expression module onto pMa5-8. The resultant plasmid was designated pMa5-gap1.

For the induced synthesis of Bsu GAPDH, an overnight culture of *E.coli* WK6, containing either pMa5-gap1 or pMc5-gap1, was diluted 100-fold in TB medium (1.2 % Bacto-tryptone; 2.4 % Bacto-yeast extract; 0.5 % glycerol; 28 mM $KH_2PO_4$; 72 mM $K_2HPO_4$) containing the appropriate antibiotic (resp. 100 μg/ml ampicillin or 25 μg/ml chloramphenicol). The cells were grown shaking at 37° C. to a density of $OD_{650nm}=1$, at which time expression of the gap gene was induced by the addition of IPTG (isopropyl-β-D-thiogalactopyranoside; 0.1 mM final concentration). The cells were harvested by centrifugation after an induction period of about 16 hours.

Under these conditions, both clones, i.e. *E.coli* WK6 (pMa5-gap1) and WK6 (pMc5-gap1) direct the efficient synthesis of a soluble 35 kD protein as apparent from the analysis of total cellular extracts on SDS-12.5% polyacrylamide gels (Laemmli, 1970). When compared to an uninduced control culture, the protein profiles of induced cultures contain a prominent 35 kD band.

The recombinant protein was present in the soluble fraction in which it was estimated to amount to at least 30 % of the total protein content. When purified, it was shown to behave identically with authentic GAPDH isolated from *Bacillus subtilis* BR151 on both native and SDS-PAGE.

The recombinant Bsu GAPDH was purified from an induced culture of *E.coli* WK6 (pMa5-gap1) (see above) as follows. Cells were washed with PBS, frozen, thawed and resuspended (200 OD/ml) in 0.1 M triethanolamine pH 7.5 containing 2 mM dithiothreitol (DTT) and 5 mM EDTA. Lysozyme was added to a final concentration of 1 mg/ml. After 20 min on ice the cells were lyzed using a French press (2×). Cell debris was removed by centrifugation. Streptomycin sulphate was added to a final concentration of 0.5%. After 1 h insoluble material was removed by centrifugation and the supernatant was made 1 mM in NAD α and subsequently 75% in ammonium sulphate. About 95% of the GAPDH activity remained in the soluble fraction. Insoluble material was removed by centrifugation. The supernatant was made 100% in ammonium sulphate and incubated at 4° C. overnight. Protein was then collected by centrifugation, and dissolved in 0.1 M triethanolamine pH 7.8 containing 1 mM DTT, 1 mM EDTA and 1 mM NAD α. Residual ammonium sulphate was removed by passage through a PD-10 (Pharmacia) desalting column equilibrated with the same buffer. The final product was at least 90% pure as assessed by SDS-PAGE.

Protein concentration was determined with the Biorad method using bovine serum albumin as a standard.

3.B. Identification of residues

The 3D-structure of Bsu GAPDH was derived from the known Bst GAPDH (Brookhaven data base pdb file pdb1gd1 —Skarzynski et al., 1987) by model building. Comparison of the primary structures of the Bsu and Bst GAPDH's (sequence of Bst GAPDH from Branlant et al., 1989) indicated that the sequences were 80% identical (FIG. 21). Therefore, the Bsu GAPDH 3D-structure could be derived using the structure of the Bst enzyme as a template.

Analysis of the 3D-structure of Bst GAPDH confirmed that the Arg-281 residues in the P and Q subunits of the Bst GAPDH form salt bridges with the Glu-201 residues in respectively subunits Q and P (Skarzynski et al., 1987). The corresponding residue in the Bsu GAPDH is Gly-282.

The 3D-structure of Bst GAPDH in the immediate neighbourhood of the Arg-281 residue in each subunit was changed by replacing all residues, having one or more atoms within a region of 10 Angstroms of these four Arg-281 residues, with the corresponding residues in the Bsu enzyme. No insertions or deletions are required. The following substitutions were performed: O_Lys-45>Gln, O_Arg-52>Lys, O_Leu-193>Tyr, O_Ser-202>Asn, O_Val-239>Leu, O_Arg-281>Gly, O_Ser-286>Asn, O_Thr-315>Ser, P_Lys-45>Gln, P_Arg-52>Lys, P_Ser-202>Asn, P_Val-239>Leu, P_Arg-281>Gly, P_Ser-286>Asn, P_Thr-315>Ser, Q_Lys-45>Gln, Q_Arg-52>Lys, Q_Ser-202>Asn, Q_Val-239>Leu, Q_Arg-281>Gly, Q_Ser-286>Asn, Q_Thr-315>Ser, R_Lys-45>Gln, R_Arg-52>Lys, R_Ser-202>Asn, R_Val-239>Leu, R_Arg-281>Gly, R_Ser-286>Asn, R_Thr-315>Ser.

The substitutions were carried out following the same procedure as outlined in Example 2 and in the order as they appear in the above list. Main chain atoms were taken from the Bst GAPDH template. The resultant modelled structure of the Bsu GAPDH can now be used to evaluate the G282K and G282R mutations. For convenience, the amino acid numbering of the Bsu GAPDH will be used throughout.

The Gly-282 residue was changed in a Lys, respectively an Arg, following the same procedure as outlined above. Table 6 summarizes the results of computations (carried out for P_Lys-282 and P_Arg-282) characterizing the intersubunit contacts involving the Lys-282 and Arg-282 residues.

The results show that, while Lys-282 is sterically accommodated (negative nonbonded energy) in the subunit interface ($ASA_b=110.4$ A), no ionic intersubunit interactions are made. The only observed intersubunit H-bond formed is with O_Glu-201.o; this would correspond to an increase in thermostability relative to the Bsu GAPDH-WT.

Arg-282 is also sterically accommodated in the subunit interface The H-bond with O_Glu-201.o is not only much stronger than observed for the Lys, but a salt bridge with the carboxylate of O_Glu-201 is also formed. Consequently, it can be expected that the electrostatic interaction between subunits will be improved, resulting in an increase of thermostability with respect to the Bsu GAPDH-G282K.

3.C. Site-directed mutagenesis of Bsu GAPDH-WT

The mutation of Gly-282 into lysine or arginine made use of a gapped DNA molecule— constructed from single stranded pMc5-gap1 (template strand) and the large StyI-ClaI fragment of pMa5-gap1 (gapped strand; see FIG. 20)— and the following oligonucleotides:

5'-GTTTCCGTTGTAGTCCTTCGAAAC-
TAATGGC-3' for introduction of a lysine, and

5'-CGTTGTAGTCGCGAGAAACTAATGG-3' for the construction of the arginine mutant.

3.D. Evaluation of the heat-inactivation of GAPDH-G282K and GAPDH-G282R with respect to GAPDH-WT

3.D.1 Enzymatic assay

The GAPDH activity of wild type and mutants was determined using a published procedure (Misset et al.,1986).

The assay mixture contained 5.6 mM glycerate-3-phosphate, 1 mM ATP, 5 mM MgSO$_4$, 1 mM EDTA, 1 mM DTT, 0.42 mM NADH, 25 μg/ml phosphoglycerate kinase (from yeast) and approximately 0.3 μg/ml GAPDH in 0.1 M triethanolamine buffer pH 7.5. All reagents were from Boehringer Mannheim. The initial rate was determined by monitoring the disappearance of NADH absorbance at 340 nm. One unit is defined as the amount of enzyme required to cause the disappearance of 1 μmol. of NADH per minute at 25° C. Specific activities were determined to be 48.4 units/mg for GAPDH-WT, 54.2 units/mg for GAPDH-G282R and 69 units/mg for GAPDH-G282K. Both mutants do not show a decrease in specific activity when compared to GAPDH-WT.

3.D.2. Heat-inactivation experiments

In the first experiment, 0.05 ml protein samples were incubated during 15 min at different temperatures. The incubation mixture contained 40 units/ml GAPDH, 1 mM DTT, 1 mM EDTA and 1 mM NAD∝ in 0.1 M triethanolamine buffer pH 7.8. The inactivation process was stopped by adding 0.45 ml of ice cold solution containing 1 mg/ml bovine serum albumin, 1 mM DTT, 1 mM NAD∝ and 1 mM EDTA in 0.1 M triethanolamine pH 7.8. Residual activity was measured and shown in FIG. 22; the temperature of 50% remaining activity was approximately 50° C. for the wild-type (GAPDH-WT), 72° C. for the GAPDH-G282K, and 75° C. for the GAPDH-G282R mutant.

The second experiment allowed to determine the rates of inactivation of these enzymes at a fixed temperature. Thus, following incubation at 74.5° C., samples were withdrawn at appropriate times. The inactivation process was stopped by ten-fold dilution in a NAD. containing bovine serum albumin solution at 0° C. and residual enzymatic activity was measured as shown in FIG. 23.

The decay obeyed first-order kinetics. The inactivation rate constant at 74.5° C. for GAPDH-G282K was 0.15 min$^{-1}$ which corresponds with a half-life of 5 min. In contrast, the rate constant for heat-inactivation at 74.5° C. for GAPDH-G282R was 0.04 min$^{-1}$, so that the half-life was increased to 18 min. The rate of heat-inactivation of GAPDH-WT could not be measured at 74.5° C., but it had a half-life of 19 min at 50° C.

In 25 mM Tris/HCl, pH 8.0, 0.2 M NaCl, SEC-HPLC on Superose-12 clearly demonstrated that GAPDH-WT elutes as a dimer, whereas both GAPDH-G282K and GAPDH-G282R eluted as tetramers. This finding is clearly in agreement with the contention that the dramatic increase in thermostability results from the introduction of intersubunit salt bridges in oligomeric proteins.

The present invention has thus been used succesfully to engineer mutations leading to more stable GAPDHs.

There follows a list of references which have been referred to above in the description of the invention and its examples with regard to known methods for achieving some of the process steps referred to herein and with regard to general knowledge which has formed the basis for this invention.

Tables referred to hereinbefore are now presented.

TABLE 1

Three and one letter codes for the twenty amino acids commonly found in proteins.

| Alanine | Ala | A | Leucine | Leu | L |
|---|---|---|---|---|---|
| Arginine | Arg | R | Lysine | Lys | K |
| Asparagine | Asn | N | Methionine | Met | M |
| Aspartic acid | Asp | D | Phenylalanine | Phe | F |
| Cysteine | Cys | C | Proline | Pro | P |
| Glutamic acid | Glu | E | Serine | Ser | S |
| Glutamine | Gln | Q | Threonine | Thr | T |
| Glycine | Gly | G | Tryptophane | Trp | W |
| Histidine | His | H | Tyrosine | Tyr | Y |
| Isoleucine | Ile | I | Valine | Val | V |

TABLE 2

Accessible surface area (ASA) for each of the 20 lysine residues of the GI monomer. Columns are, from left to right, position of lysine residues in the primary sequence (K), ASAs in the isolated subunit (ASA$_M$), ASAs in the GI tetramer (ASA$_T$) and area buried within subunit interfaces (A$_b$ = ASA$_M$ − ASA$_T$) in the assembled tetramer.

| K | ASA$_M$ | ASA$_T$ | A$_b$ |
|---|---|---|---|
| 10 | 65.4 | 65.4 | 0.0 |
| 42 | 52.6 | 52.6 | 0.0 |
| 76 | 77.1 | 77.1 | 0.0 |
| 77 | 142.4 | 142.4 | 0.0 |
| 100 | 150.0 | 0.8 | 149.2 |
| 118 | 17.9 | 6.8 | 11.1 |
| 132 | 147.4 | 147.4 | 0.0 |
| 149 | 6.9 | 3.2 | 3.7 |
| 183 | 8.0 | 0.1 | 7.9 |
| 239 | 167.0 | 167.0 | 0.0 |
| 240 | 19.2 | 18.1 | 1.1 |
| 253 | 111.5 | 1.5 | 110.0 |
| 294 | 51.5 | 28.7 | 22.8 |
| 309 | 93.2 | 93.2 | 0.0 |
| 319 | 30.0 | 30.0 | 0.0 |
| 323 | 83.0 | 83.0 | 0.0 |
| 339 | 78.0 | 50.3 | 27.7 |
| 344 | 178.1 | 125.8 | 52.3 |
| 375 | 132.0 | 119.2 | 12.8 |
| 381 | 114.2 | 67.7 | 46.5 |

TABLE 3

Catalytic parameters of wild-type (WT) and mutant EcoAmi(DSM) GI with either D-xylose (coupled assay) or D-glucose as substrates.

| | Xylose | | | Glucose | |
|---|---|---|---|---|---|
| | Spa | Vmax | Km | Vmax | Km |
| WT-GI | 24.5 | 24.2 | 4.8 | 30.6 | 217 |
| K253R | 30.0 | 24.6 | 5.3 | 27.2 | 177 |
| K253Q | 23 | 15.1 | 4.4 | 29.0 | 210 |
| K100R | 22.2 | ND | ND | ND | ND |

Spa = specific activity in micromoles of product (D-xylulose or D-fructose) per minute (unit), per mg of enzyme.
V$_{MAX}$ is expressed in units per mg of enzyme.
K$_M$ is the Michaël is constant, expressed in mM.
ND = not determined.

TABLE 4

Half-life in hours for wild type (WT-GI) and mutant (K253R) GI. The half-life is the time required to reduce total enzymatic activity by 50%. The buffer used was 50 mM EPPS, pH 7.5 at 84° C., 5 mM MgSO$_4$.

| T (°C.) | 82 | 84 | 86 | 88 | 90 | 92 |
|---|---|---|---|---|---|---|
| WT-GI | 11.85 | 3.80 | 1.07 | 0.25 | 0.080 | 0.032 |
| K253R | 17.65 | 4.17 | 1.11 | 0.30 | 0.094 | 0.037 |

TABLE 5

Analysis of 3D-structure of human CuZnSOD as derived from the bovine structure (see text). NE: nonbonded energy. Notation of the hydrogen bonds follows the UPAC Convention (In Proteins, 1976, (G. D. Fastman, ed.), CRC Critical Reviews in Biochemistry 1:59-90)

| | O—Lys-9 | O—Arg-9 |
|---|---|---|
| NE (kcal mol) | −13.5 | −23.5 |
| H-bonds distance in Å) | .h..O144—Cys.o (2.02) | .h...O144—Cys.o (2.02) |
| | .hz1..O8—Leu.o (2.48) | .o..O144—Cys.h (2.13) |
| | .hz2..O8—Leu.o (2.04) | .hh11..O14—Val.o (2.14) |
| | .o..O144—Cys.h (2.13) | .hh12..O12—Gly.o (2.23) |
| | | .hh22..O12—Gly.o (1.82) |

| | O—Lys-122 | O—Lys-128 |
|---|---|---|
| NE (kcal/mol) | −0.15 | −3.4 |
| H-bonds (distance) in Å | .hz2..O137—Asn.o (2.16) | none |
| | .hz2..O138—Val.o (2.47) | |
| | .o..O42—Gly.h (2.03) | |

| | O—Arg-122 | O—Arg-128 |
|---|---|---|
| NE (kcal/mol) | −7.5 | −9.1 |
| H-bonds (distance in Å) | .he...O138—Ala.o (2.45) | .he..O125 Gly.o (1.96) |
| | .hh12..O119—Glu.oe1 (2.69) | |
| | .hh22..O119—Glu.oe1 (2.39) | |
| | .o...O42—Gly.h (2.03) | |

TABLE 6

Analysis of 3D-structure of Bsu GAPDH as derived from the structure of Bst GAPDH (see text). NE: nonbonded energy: $ASA_T$ and $ASA_M$: accessible surface area in respectively tetramer and monomer; $ASA_b$: buried surface. Notation of the hydrogen bonds follow the UPAC Convention (In Proteins, 1976, (G. D. Fastman, ed.), CRC Critical Reviews in Biochemistry 1:59-90)

| | P—Lys-282 | P—Arg-282 |
|---|---|---|
| $ASA_M$ (Å) | 22.2 | 34.7 |
| $ASA_T$ (Å) | 132.6 | 148.8 |
| $ASA_b$ (Å) | 110.4 | 114.1 |
| NE (kcal/mol) | −18.64 | −31.3 |
| H-bonds (distance in Å) | .hz1..OP407—Hoh.o (1.86) | .he..O201—Glu.o (1.83) |
| | .hz2..OP429—Hoh.o (1.94) | .hh11..OR408—Hoh.o (2.67) |
| | .hz2..O201—Glu.o (2.30) | .hh12..OP534—Hoh.o (2.62) |
| | o..P284—Asn.h (2.23) | .hh22..Q201—Glu.oe1 (1.77) |
| | | .o..P284—Asn.h (2.23) |

TABLE 7

Residual activity (%) of SOD-WT and SOD-K122R/K128R in the absence or presence of glucose (0.1 M) at 60° C. in 0.2 M potassium phosphate, pH 7.35. Enzymes were produced by sodAsodB⁻ E. coli (see text).

| | [Glucose] | 14 hours | 18 hours | 22 hours |
|---|---|---|---|---|
| SOD-WT | | | | |
| | none | 100 | 72 | 84 |
| | 0.1 M | 72 | 30 | 0 |
| SOD-K122R/K128R | | | | |
| | none | 100 | 100 | 98 |
| | 0.1 M | 100 | 57 | 30 |

REFERENCES

AHERN, T. J. and KLIBANOV, A. M. (1985) Science 228: 1280–1284.

AHERN, T. J., CASAL, J. I., PETSKO, G. A. and KLIBANOV, A. M. (1987) Proc. Natl. Acad. Sci. USA 84: 675–679.

ALBER, T. A., DAO-PIN, S., NYE, J. A., MUCHMORE, D. C. and MATTHEWS, B. W. (1987) Biochemistry 26: 3754–3758.

ANFINSEN, C. B. and SHERAGA, H. A. (1975) Adv.Prot.Chem. 29: 205–299.

ARAI K., IIZUKA S., TADA Y., OIKAWA K. and TANIGUCHI N. (1987 a) Biochem.Biophys.Acta 924:292–296

ARAI K., MAGUCHI S., FUJII S., ISHIBASHI H., OIKAWA K. and TANIGUCHI N. (1987 b) J.Biol.Chem. 262:16969–16972

ARGOS P. (1989) J.Mol.Biol. 206:397–406

BALDWIN, R. L. (1986) Proc. Natl. Acad. Sci. USA, 83: 8069–8072.

BANNISTER J. V., BANNISTER W. H. and ROTILIO G. (1987) CRC Crit.Rev.Biochem. 22:111–180

BEAUCAGE S. J. and CARUTHERS M. H. (1981) Tetrahedron Letters 22:1859–1862.

BEAUCHAMP C. and FRIDOVICH I. (1971) Anal. Biochem. 44:276–287

BERGMEYER, H. V. (1983) in "Methods in Enzymatic Analysis", vols I-XII, Verlag Chemie, Weinheim, FRG.

BERNSTEIN, F. C. et al. (1977) J. Mol. Biol. 112: 532–542.

BIESECKER G., HARRIS J. I., THIERRY J., WALKER J. E. and WONACOTT A. J. (1977) Nature 266:328–333

BOTTERMAN, J. and ZABEAU, M. (1987) DNA 6: 583–591.

BOOKCHIN, R. M. and GALLOP, P. M. (1968) Biochem. Biophys.Res. Commun. 32: 86–93.

BRANLANT C., OSTER T. and BRANLANT G. (1989) Gene 75:145–155

BUNN, H. F., HANEY, D. N., GABBAY, K. N. and GALLOP, P. M. (1975) Biochem. Biophys. Res. Commun. 67: 103–109.

BUNN, H. F., GABBAY, K. N. and GALLOP, P. M. (1978) Science 200: 21–27.

CARLIOZ A. and TOUATI D. (1986) EMBO J. 5:623–630

CASAL, J. I., AHERN, T. J., DAVENPORT, R. C., PETSKO, G. A. and KLIBANOV, A. M. (1987) Biochemistry 26: 1258–1264.

CHOTHIA, C. and JANIN, J. (1976) Nature 256: 705–708.

COCCO D., ROSSI L., BARRA D., BOSSA F. and ROTILIO G. (1982) FEBS Lett. 150:303–306

COLSON C., GLOVER S. W., SYMONS N. and STACEY K. (1965) Genetics 52: 1043–1050.

CREIGHTON, T. E. (1988) BioAssays 8 : 57–63.

CREIGHTON, T. E. (1983) in "Proteins, Structures and Molecular Principles", Freeman, N.Y.

DE BOER H. A., COMSTOCK L. J. and VASSER M. (1983) PNAS

DELHAISE, P., VAN BELLE D., BARDIAUX, M. and WODAK, S. (1984) J. Mol. Graph. 3: 116–119.

DILL, K. A. (1987) Prot. Engineer. 1: 369–372.

DISCHE, Z., and E. BORENFREUND (1951) J. Biol. Chem 192: 583–587.

DODET, B. (1987) La Recherche 18: 658-668.

FERSHT, A. R. (1985) in "Enzyme Structure and Mechanism", Freedman, H. W., New york.

FLETCHER, R. and REEVES, C. M. (1964) Comput. J. 6:163-168.

FLETCHER, R. and REEVES, C. M. (1966) Comput. J. 7: 149-158.

GODFREY, T. and REICHELT, J. (1983) in "Industrial Enzymology", Stockton Press.

GOLDBERG, M. E. (1969) J. Mol. Biol. 46: 441-446.

GOTTSCHALK, N. and JAENICKE, R. (1987) Biotechnol. Appl. Biochem. 9: 389-400.

HALLEWELL R. A. et al. (1985) Nucl.Acids Res. 13:2017-2034

HALLEWELL R. A. et al. (1989) J.Biol.Chem. 264:5260-5268

HARTLEY R. W. (1988) J.Mol.Biol. 202:913-915

HARTZ J. W. and DEUTSCH H. F. (1972) J.Biol.Chem. 21:7043-7050

HIGGINS, P. J. and BUNN, H. F. (1981) J. Biol. Chem. 256: 5204-5208.

HOL, W. G., 1985, Progr. Bioph. Mol. Biol. 45: 149-195.

HOLMQUIST, W. R. and SCHROEDER, W. A. (1964) Biochem. Biophys. Res. Commun. 32: 639-641.

HOWARD-FLANDERS P., BOYCE R. P. and L. THERIOT (1966) Genetics 53:1119-1136.

INGLIS, A. S. (1983) Meth. Enzymol. 91: 324

JAENICKE, R. (1987) Prog. Biophys. molec. Biol. 49: 117-237.

JANIN, J. (1979) Bull. Inst. Pasteur (Paris) 77: 337-374.

JANIN, J. and WODAK, S. J. (1983) Prog. Biophys. molec. Biol. 42: 21-78.

KAUZMANN, W. (1959) Adv. Prot. Chem. 14: 1-63.

KERSTERS-HILDERSON et al. (1987) Enzyme Microb. Technol. 9 : 145-148.

KLIBANOV, A. M. (1983) Adv. Appl. Microbiol. 29: 1-28.

KNOWLES, J. R. (1987) Science 236: 1252-1258.

KOENIG, R. J., BLOBSTEIN, S. H. and CERAMI, A. (1977) J. Biol. Chem. 252: 2992-2997.

KYTE, and DOOLITTLE, (1982) J. Mol. Biol. 157: 105-132.

LAEMMLI, U. K. (1970) Nature 227: 680-685.

LEE, B. K. and RICHARDS, F. M. (1971) J. Mol. Biol. 55: 379-400.

MANIATIS, T., FRITSCH, E. F. and SAMBROOK, J. S. (1982) in "Molecular Cloning: A laboratory Manual", Cold Spring Harbor Laboratory, Cold Spring Harbor, N.Y.

MARKLUND S. AND MARKLUND G. (1974) Eur. J. Biochem. 47:469-474

MARMOCCHI F., MAVELLI I., RIGO A., SREVANATO R., BOSSA F. and ROTILIO G. (1982) Biochem. 21:2853-2856

MATSUMURA, M., BECKTEL, W. J. and MATTHEWS, B. W. (1988) Nature 334: 406-410.

MATTHEWS, B. W., NICHOLSON, H. and BECKTEL, W. J. (1987) Proc. Natl. Acad. Sci. USA 84: 6663-6667.

MAXAM, A. M. and GILBERT, W. (1980) Meth. Enzymol. 65: 499-559.

MILLER, J. H. (1972) in "Experiments in Molecular Genetics", Cold Spring Harbor Laboratory, Cold Spring Harbor, N.Y.

MILLER S., LESK A. M. and J.JANIN (1987) Nature 328: 834-835.

MISSET O., BOS O. J. M. and OPPERDOES F. R. (1986) Eur.J.Biochem. 157:441-453

MORAS D., OLSEN K. W., SABESAN M. N., BUEHNER M., FORD G. C. and ROSSMAN M. G. (1975) J.Biol.Chem. 250:9137-9162

MRABET, N. T., SHAEFFER, J. R., McDONALD, M. J. and BUNN, H. F. (1986) J. Biol. Chem. 261: 1111-1115.

PANTOLIANO, M. W., LADNER, R. C. , BRYAN, P. N., ROLLENCE, M. L., WOOD, J. F. and POULOS, T. L. (1987) Biochemistry 26: 2077-2082.

PERRY, L. J. and WETZEL, R. (1984) Science 226: 555-557.

PERUTZ M. F. (1978) Nature 201: 1187-1191.

PORTER, R. R. (1973) Science 180: 713-716.

PRIVALOV, P. L. (1979) Adv. Prot. Chem. 33: 167-241.

PTITSYN, O. B. (1987) J. Prot. Chem. 6: 273-293.

REY F., JENKINS, J., JANIN J., LASTERS I., ALARD P., CLAESSENS M., MATTHYSSENS G. and WODAK S. (1988) Proteins 4:165-172

ROSE, G. D. (1979) J. Mol. Biol. 134: 447-470.

ROSE, G. D., GESELOWITZ, A. R., LESSER, G. J., LEE, R. H. and ZEHFUS, M. H. (1985) Science 229: 834-838.

ROSKAM, W. (1987) La Recherche 18: 646-656.

RUSSEL et al. (1987) J. Mol. Biol. 193: 803

SADANA and HENLEY (1986) Biotechnol. Bioeng. 28: 256-268.

SAUER, R. T., HEHIR, K., STEARMAN, R. S., WEISS, M. A., JEITLER-NILSSON, A., SUCHANEK, E. G. and PABO, C. O. (1986) Biochemistry 25: 5992-5998.

SKARZYNSKI T., MOODY P. C. E. and WONACOTT A. J. (1987) J.Mol.Biol. 193:171-187

STANSSENS, P., McKEOWN, Y., FRIEDRICH, K. and FRITZ, H.-J. (1987) in "Oligonucleotide-directed construction of mutations by the gapped duplex DNA method using the pMa/c plasmid vectors", Manual used at the EMBO laboratory course, "Directed Mutagenesis and Protein Engineering" held at the Max Planck Institüt für Biochemie, Martinsried, Jul. 4-18, 1987.

TAINER J. A., GETZOFF E. D., BEEM K. M., RICHARDSON J. S. and RICHARDSON D. C. (1982) J.Mol.Biol. 161:181-217

TAYLOR W. R. (1988) Protein Engineering 2:77-86.

TORCHILIN et al. (1983) J. Mol. Catal. 19: 291-301.

VAN BEYNUM and ROELS, eds. (1985) in "Starch Conversion Technology", Marcel Dekker, Inc.

VIAENE A., BAUW G., VAN KAERT L., VANDEKERCKHOVE J., VAN MONTAGU M. and DHAESE P. (1988) Arch.Int.Physiol.Biochem. 96:B197

VIAENE A. and DHAESE P. (1989) Nucl.Acids Res. 17:1251

VILLAFRANCA, J. E., HOWELL, E. E., OATLEY, S. J., XUONG, N. and KRAUT, J. (1987) Biochemistry 26: 2182-2189.

VILLAFRANCA, J. E., HOWELL, E. E., VOET, D. H., STROBEL, M. S., OGDEN, R. C. , ABELSON, J. N. and KRAUT, J. (1983) Science 222: 782-788.

WALKER J. E., WONACOTT, A. J. and HARRIS, J. I. (1980) Eur. J. Biochem. 108: 581-586.

WATSON, J. D., TOOZE, J. and KURTZ, D. T. in "Recombinant DNA", Freeman & Co.

WELLS, J. A. and POWERS, D. B. (1986) J. Biol. Chem. 261: 6564–6570.
WELLS, J. A., POWERS, D. B., BOTT, R. R., GRAYCAR, T. P. and ESTELL, D. A. (1987) Proc. Natl. Acad. Sci. USA 84: 1219–1223.
WETLAUFER, D. B. (1973) Proc. Natl. Acad. Sci. USA 70: 697–701.
WETZEL, R. (1985) Eur. pat. applic. #8530129.9.
WETZEL, R. (1987) TIBS 12: 478–482.
WIGLEY, D. B., LYALL, A., HART, K. W. and HOLBROOK, J. J. (1987) Biochem. Biophys. Res. Comm. 149: 927–929.
WINNACKER E.-L. (1987) "From Genes to Clones" VCH Publishers, N.Y.
WINTERBOURN C. C., HAWKINS R. E., BRIAN M. AND CARREL R. W. (1975) J. Lab. Clin. Med. 85:337–341
WODAK, S, and JANIN J. (1981) Biochemistry 20: 6544–6552
WUTHRICH, K. (1986) in "NMR of Proteins nd Nucleic Acids", J. Wiley & sons.
WYCKOFF, H. W., HIPS, C. H. W. and VAN VUNAKIS, H., eds (1985) in "Diffraction Methods for Biological Macromolecules", Meth. Enzymol. Vols 114–115, Acad. Press.
YAMANAKA, K. (1971) Bull. Yamaguchi Med. School 18: 1–5.
YANNISCH-PERRON C., VIEIRA J. and MESSING J. (1985) Gene 33:103–119
YOUNG F. E. et al. (1969) J.Bacteriol. 98:1087
ZALE, S. E. and KLIBANOV, A. M. (1986) Biochemistry 25: 5432–5444.

For additional definitions of expressions used in the present application—and to the extent they are not largely made clear in the literature made of record hereabove—reference can also be made to the book titled "Molecular Biology of the Gene", fourth edition of James D. Watson, Nancy H. Hopkins, Jeffrey W. Roberts, Joan Argetsinger Slitz and Alan M. Weiner, (1987) published by the Benjamin/Cummings Publishing Company, Inc.

When reference is made hereinafter, in the claims to a "naturally occurring protein or mutant thereof", it must be understood 1) that "naturally occurring protein" means both a protein which occurs in nature as such or a protein having the same basic amino acid sequence as obtained by man-contrived techniques, e.g., genetic engineering techniques;

2) that mutant thereof may be any variant thereof having essentially the same biological properties in kind and deriving in effect of a possible mutation in the corresponding gene, except that the relevant lysine or arginine residue which is to undergo substitution has not been affected by that particular mutation.

We claim:

1. A method to enhance the stability of a superoxide dismutase enzyme to chemical modification, without destroying the catalytic activity of said enzyme, which method comprises replacing at least one lysine residue in the primary structure of said enzyme with an arginine residue,
   wherein said lysine residue has been identified as not associated with the catalytic activity of said enzyme;
   wherein said lysine residue has been identified as located at a site that can sterically accommodate the substitution of an arginine residue;
   wherein said lysine residue occurs within an interface between domains or subunits; and
   wherein said lysine residue is located at a site of high accessible surface area.

2. The method of claim 1 wherein said enzyme which is modified by having at least one lysine residue replaced is CuZn superoxide dismutase.

3. A method to enhance the thermal stability of an enzyme, without destroying the catalytic activity of said enzyme which is selected from the group consisting of superoxide dismutase and glyceraldehyde phosphate dehydrogenase, which method comprises
   1) replacing in superoxide dismutase at least one lysine residue in the primary structure of said enzyme with an arginine residue,
      wherein said lysine residue has been identified as not associated with the catalytic activity of the enzyme;
      wherein said lysine residue has been identified as located at a site that can sterically accommodate the substitution of an arginine residue;
      wherein said lysine residue has been identified as participating in electrostatic interactions at an interface between subunits or domains; and
      wherein said lysine residue has been identified as at a site of low accessible surface area; or
   2) replacing in glyceraldehyde phosphate dehydrogenase at least one glycine residue with a lysine or arginine residue;
      wherein said glycine residue has been identified as not associated with the catalystic activity of said enzyme;
      wherein said glycine residue occurs within an interface between domains or subunits; and
      wherein said glycine residue is located at a site of high accessible surface area.

4. A method of claim 3 wherein said enzyme which is modified by having at least one glycine replaced is glyceraldehyde phosphate dehydrogenase.

5. DNA that encodes a modified superoxide dismutase enzyme the modified enzyme having enhanced stability to chemical modification as compared to the native enzyme, without destroying the catalytic activity of said native enzyme, or an expression system for said DNA operable in a recombinant host cell, which modification comprises replacing at least one codon in the DNA which encodes a lysine residue in the primary structure of said enzyme with a codon which encodes an arginine residue,
   wherein said lysine residue has been identified as not associated with the catalytic activity of said enzyme;
   wherein said lysine residue has been identified as located at a site that can sterically accommodate the substitution of an arginine residue;
   wherein said lysine residue occurs within an interface between domains or subunits; and
   whereins aid lysine residue is located at a site of high accessible surface area.

6. The DNA of claim 5 wherein said modified enzyme is modified CuZn superoxide dismutase.

7. Recombinant host cells transformed with an expression system containing the DNA of claim 5.

8. A method to produce a modified enzyme with enhanced stability to chemical modification as compared to the native enzyme which method comprises culturing the cells of claim 7 under conditions wherein said DNA is expressed to produce modified said enzyme; and recovering said modified enzyme from the culture.

9. A recombinant or synthetic DNA that encodes a modified enzyme selected from the group consisting of a modified superoxide dismutase and a modified glyceraldehyde phosphate dehydrogenase, the modified enzyme having enhanced thermal stability as compared to the native enzyme, without destroying the catalystic activity of said native enzyme, recombinant or synthetic DNA that encodes a modified enzyme, which modification comprises 1) replacing in superoxide dismutase at least one codon in the DNA which encodes a lysine residue in the primary structure of said enzyme with a codon which encodes an arginine residue, wherein said lysine residue has been identified as not associated with the catalytic activity of the enzyme;

wherein said lysine residue has been identified as located at a site that can sterically accommodate the substitution of an arginine residue;

wherein said lysine residue has been identified as participating in electrostatic interactions at an interface between subunits or domains; and wherein said lysine residue has been identified as at a site of low accessible surface area; or 2) replacing in glyceraldehyde phosphate dehydrogenase at least one codon which encodes a glycine residue with a codon which encodes a lysine or arginine residue;

wherein said glycine residue has been identified as not associated with a catalytic activity of said enzyme;

wherein said glycine residue occurs within an interface between domains or subunits; and wherein said glycine residue is located at a site of high accessible surface area.

10. The DNA of claim 9 wherein said modified enzyme is modified glyceraldehyde phosphate dehydrogenase.

11. Recombinant host cells transformed with an expression system containing the DNA of claim 9.

12. A method to produce a modified enzyme with enhanced stability to chemical modification as compared to the native enzyme which method comprises culturing the cells of claim 11 under conditions wherein said DNA is expressed to produce said modified enzyme; and recovering said modified enzyme from the culture.

* * * * *